US008962140B2

(12) United States Patent
Müller et al.

(10) Patent No.: US 8,962,140 B2
(45) Date of Patent: Feb. 24, 2015

(54) FUNCTIONALIZED CORE-SHELL NANOPARTICLES

(71) Applicant: BASF SE, Ludwigshafen (DE)

(72) Inventors: Martin Müller, Lorrach (DE); Didier Bauer, Kembs (FR); Thomas Ruch, Delemont (CH); Leonhard Feiler, Binzen (DE); Wolfgang Schlenker, Aesch (CH); Christian Cremer, Lorrach (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/705,389

(22) Filed: Dec. 5, 2012

(65) Prior Publication Data
US 2013/0096241 A1 Apr. 18, 2013

Related U.S. Application Data

(63) Continuation of application No. 12/598,767, filed as application No. PCT/EP2008/055040 on Apr. 25, 2008, now abandoned.

(30) Foreign Application Priority Data

May 11, 2007 (EP) .................................. 07108002
Oct. 19, 2007 (EP) .................................. 07118846

(51) Int. Cl.
| | | |
|---|---|---|
| *B32B 5/16* | (2006.01) | |
| *B05D 7/00* | (2006.01) | |
| *C08K 5/5455* | (2006.01) | |
| *C07F 7/18* | (2006.01) | |
| *B82Y 30/00* | (2011.01) | |

(52) U.S. Cl.
CPC ........... *C08K 5/5455* (2013.01); *C07B 2200/11* (2013.01); *C07F 7/1836* (2013.01); *B82Y 30/00* (2013.01); *Y10S 977/773* (2013.01)
USPC ........... 428/403; 427/214; 427/215; 427/220; 427/221; 428/407; 428/447; 977/773

(58) Field of Classification Search
USPC .......... 428/403–407, 447; 427/212, 215, 220, 427/221; 997/773
See application file for complete search history.

(56) References Cited

U.S. PATENT DOCUMENTS

| | | | |
|---|---|---|---|
| 4,877,451 A | 10/1989 | Winnik et al. | |
| 5,209,998 A | 5/1993 | Kavassalis et al. | |
| 7,226,647 B2 | 6/2007 | Kasperchik et al. | |
| 7,794,509 B2 | 9/2010 | Cremer et al. | |
| 2003/0194715 A1 | 10/2003 | Li et al. | |
| 2004/0204521 A1* | 10/2004 | Camenzind et al. | 524/90 |
| 2005/0059766 A1 | 3/2005 | Jones et al. | |
| 2006/0183246 A1 | 8/2006 | Wiesner | |
| 2009/0076198 A1 | 3/2009 | Giesenberg | |
| 2009/0099282 A1 | 4/2009 | Muller | |
| 2009/0100610 A1 | 4/2009 | Cremer | |
| 2009/0130045 A1 | 5/2009 | Cremer | |
| 2009/0151091 A1 | 6/2009 | Cremer | |
| 2009/0217465 A1 | 9/2009 | Cremer | |
| 2009/0229059 A1 | 9/2009 | Cremer | |
| 2009/0255063 A1 | 10/2009 | Marquais-Bienewald | |
| 2010/0162494 A1* | 7/2010 | Muller et al. | 8/636 |
| 2010/0192312 A1 | 8/2010 | Cremer et al. | |
| 2010/0317819 A1* | 12/2010 | De Keyzer et al. | 528/33 |

FOREIGN PATENT DOCUMENTS

| | | |
|---|---|---|
| EP | 1883676 A1 | 2/2008 |
| WO | 2004063387 A2 | 7/2004 |
| WO | 2006125736 A1 | 11/2006 |

OTHER PUBLICATIONS

Kecht et al., Selective functionalization of the outer and inner surfaces in mesoporous silica nanoparticles, Chem. Mater., 2008, 20 (23), 7207-7214 (Available online Nov. 14, 2008).*

* cited by examiner

*Primary Examiner* — Holly Le
(74) *Attorney, Agent, or Firm* — Shruti Costales

(57) ABSTRACT

Functionalized nanoparticles, which are obtainable by combining in a first step a functionalized dyestuff, a silicon-based spacer and a catalyst, and in a second step reacting the product obtained in the first step with a co-reactive organic silicon, aluminum, zirconium or titanium compound. Optionally, the thus obtained functionalized nanoparticles can be combined or encapsulated with a polymer. The functionalized nanoparticles are useful as colorants and fluorescents in plastics, paints, inks, electronic materials, cosmetic articles, and the like.

9 Claims, No Drawings

FUNCTIONALIZED CORE-SHELL NANOPARTICLES

The invention relates to functionalized nanoparticles, its preparation and use.

Colorant and fluorescent nanoparticles are highly recommended in decorative, electronic, industrial, security and home and personal care markets delivering effects to the customers. These applications require stabilized, migration free and heat resistant fluorescents and colorants that can be specifically modified like pigments to adapt on desired applications.

However, the fluorescent signal from a solid dyestuff is weak, and the dye molecules in solid, in solvent or polymer matrix are susceptible to migration, decomposition by heat and irreversible photodegradation. It is a known fact that almost all fluorescent dyes in application (solution, polymer, paint, ink or matrix) are self-quenching if the concentration of dye gets high enough. This means, that the dye itself decreases the fluorescence intensity by promoting decay from the excited state without emitting a photon.

Different approaches have emerged in recent years for synthesizing fluorescent materials for use in a range of demanding applications. In the first approach, the fluorescent dye is linked to a polymer matrix. In the second, the fluorescent dye is encapsulated in a polymer matrix ba at least on kind of polymer prior to the end application to prevent dye molecules as good as possible from migration and self quenching. In addition, in order to avoid e.g. swelling or porosity change with pH changes, agglomeration in aqueous medium etc. that are associated with the above two approaches, silica nanoparticles had been manufactured with an embedded dye. In all reports, water/alcohol soluble dyes such as fluoresceine or rhodamine were used and the dye load was low in order to avoid fluorescence self-quenching.

E.g. WO 2004/063387 A2 discloses fluorescent silica-based nanoparticles comprising a core with a fluorescent silane compound and a silica shell on this core. In particular, a reactive fluorescent compound such as a dye is reacted with a co-reactive organo-silane to form a fluorescent core particle. This fluorescent core particle is further treated with a silica forming compound to form a silica shell on the core. A disadvantage of the thus produced particles is that the absorption is not high enough for some applications, and that migration leads to bleeding if applied in e.g. plastics or paper.

It was therefore an objective of present invention to increase the quantum yield of fluorescent nanosized particles and to decrease the effect of bleeding.

Accordingly functionalized nanoparticles were found, which are obtainable by a) combining a functionalized dyestuff of the formula (1a)

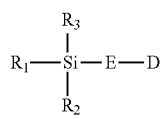

(1a)

wherein
$R_1$ stands for $C_1$-$C_{18}$alkoxy, —OH;
$R_2$, $R_3$ independently from each other stand for $C_1$-$C_{18}$alkoxy or $C_1$-$C_{18}$alkyl, —OH,
E stands for a direct bond or a bridging member, preferably for $C_1$-$C_{24}$alkylene,
$C_6$- or $C_{12}$aryl, or $(C_6$-)ar$(C_{1-4})$alkylene,
D is the residue of a chromophore,
and a spacer of the formula (1b)

$$R_{4(4-m)}SiX_m \qquad (1b)$$

wherein each
$R_4$ represents a monovalent organic radical of from 1 to 24 carbon atoms, optionally substituted by a monovalent organic radical,
X represents a group capable of undergoing hydrolysis and m is 0, 1, 2, 3 or 4;
a catalyst,
and optionally a solvent, at time $T_{SB}$,
and treating the obtained mixture until time $T_{SE}$, wherein $(T_{SE}-T_{SB})$ is chosen in the range of from 1 and 48 hours, at a temperature in the range of from 0 to 80° C., b) adding a co-reactive compound (1c) selected from the group consisting of an organic silane,
an organic alumina, an organic zirconia and an organic titania, at time $T_{CC}$, wherein $T_{CC}$ fulfils condition (a) $T_{CC} \geq T_{SE}$, (b) $T_{SB} < T_{CC} < T_{SE}$, or
(c) $T_{SB} < T_{CC1} < T_{SE} \leq T_{CC2}$ in case part of co-reactive compound (1c) is added before $T_{SE}$, and the other part after $T_{SE}$, and treating the obtained respective reaction mixture for a period of time between 12 and 36 hours at a temperature between 0 and 80° C.,
and, optionally, after isolating the thus obtained nanoparticles with well-known methods, c) combining the nanoparticles with a polymer or, d) polymerizing a monomer or monomer mixture in the presence of the nanoparticles.

The functionalized dyestuffs (1a) can be prepared in analogy to known processes, in which a reactive chromophore is reacted with a co-reactive organo-silane compound to form the functionalized dyestuff (1a).

The chromophore thus can be linked by any known chemical coupling methods using e.g. carboxylates, anhydrides, esters, alcohols, thiols, carbamides, aldehydes, amines, sulfur oxides, nitrogen oxides, halides or carbodiimide coupling as well as e.g. addition reaction and ring-opening reactions.

As will be clear to one skilled in the art, suitable protecting groups can be used during the ligation reaction. For example, other functional groups present in the reactive organic compound or co-reactive organo-silane can be partially or completely be removed to provide the ligated-compounds, ie preferably a organo-silane dyestuff. Suitable protecting groups and methods for their incorporation and removal are well known in the art (see for example Green, T. W.; Wutz, P. G. M. "Protecting Groups In Organic Synthesis" $2^{nd}$ edition, 1991, New York, John Wiley & Sons, Inc.).

Additionally, when a carboxylic acid is reacted with a hydroxyl group, a mercapto group, or an amine group to provide an ester linkage, thioester linkage, or an amide linkage, the carboxylic acid can be activated prior to the reaction, for example, by formation of the corresponding acid chloride. Numerous methods for activating carboxylic acids, and for preparing ester linkages, thioester linkages, and amide linkages, are known in the field (see for example, "Advanced Organic Chemistry: Reaction Mechanisms and Structure, $4^{th}$ ed., Jerry March, John Wiley & Sons, pages 419 to 437, and 1281).

Reactive chromophores are well-known for example from "Molecular Probes Handbook of Fluorescent Probes and Research Chemicals", 6th ed., R. P. Haugland, ed. (1996). A typical chromophore is e.g. a aromatic or heteroaromatic compound such as is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a porphycene, a salicylate, an anthranilate, an azulene, a perylene, a pyridine, a quinoline, a coumarin (including hydroxycoumarins and aminocoumarins and fluorinated derivatives thereof), naphthalimide, rhodamine, fluoresceine, stilbene, xanthene, and benzoxanthenes and like compounds, see for example U.S. Pat. Nos. 5,830,912; 4,774,339; 5,187,288; 5,248,782; 5,274,113; 5,433,896; 4,810,636; and 4,812,409.

As co-reactive organo-silane silanes of the general formula

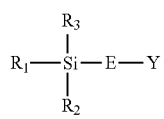
(1a')

can be used, where
$R_1$ stands for $C_1$-$C_{18}$alkoxy, —OH;
$R_2$, $R_3$ independently from each other stand for $C_1$-$C_{18}$alkoxy or $C_1$-$C_{18}$alkyl, —OH,
E stands for $C_1$-$C_{24}$alkylene, $C_6$- or $C_{12}$aryl, or $(C_6$-$)ar(C_{1-4})$alkylene,
Y is a leaving group, e.g. a hydrolyzable group such as $C_1$-$C_4$alkoxy, which can be substituted by $C_1$-$C_4$alkoxy; —NCO, NCS, —SH, halogen, —$NH_2$, $NHR_5$, $NR_6R_7$, wherein $R_5$, $R_6$, $R_7$ independently from each other stand for $C_1$-$C_{18}$alkyl, or amino-$C_1$-$C_{18}$alkyl.

$C_1$-$C_{18}$alkoxy stands for methoxy, ethoxy, n-, i-propoxy, n-, i-, sec.-, tert.-butoxy, n-pentoxy, n-hexoxy, n-heptoxy, n-octoxy, n-nonoxy, n-decoxy, n-undecoxy, n-dodecoxy, n-tridecoxy, n-tetradecoxy, n-pentadecoxy, n-hexydecoxy, n-heptydecoxy, n-octadecoxy, preferably for $C_1$-$C_4$alkoxy such as for methoxy, ethoxy, n-propoxy, n-butoxy.

$C_1$-$C_4$alkoxy group, which is substituted by $C_1$-$C_4$alkoxy can be e.g. 2-methoxy-ethoxy, 2-methoxy-ethoxy-2-ethoxy.

$C_1$-$C_{18}$alkyl stands for methyl, ethyl, n-, i-propyl, n-, i-, sec.-, tert.-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexydecyl, n-heptydecyl, n-octadecyl, preferably for $C_1$-$C_4$alkyl such as for methyl, ethyl, n-propyl, n-butyl.

$C_1$-$C_{24}$alkylene stands for methylene, ethylene, n-, i-propylene, n-, i-, sec.-, tert.-butylene, n-pentylene, n-hexylene, n-heptylene, n-octylene, n-nonylene, n-decylene, n-undecylene, n-dodecylene, n-tridecylene, n-tetradecylene, n-pentadecylene, n-hexydecylene, n-heptydecylene, n-octadecylene, n-nonadecylene, n-eicosylene, n-uneicosylene, n-doeicosylene, preferably $C_1$-$C_8$alkylene such as methylene, ethylene, n-, i-propylene, n-, i-, sec.-, tert.-butylene, n-pentylene, n-hexylene, n-heptylene, n-octylene, particularly preferred $C_1$-$C_4$alkylene such as methylene, ethylene, n-, i-propylene, n-, i-, sec.-, tert.-butylene.

$C_6$- or $C_{12}$aryl stands for phenylene or naphthylene, e.g. o-phenylene, m-phenylene, p-phenylene,
$C_6$ar-$C_{1-4}$alkylene stands for —$(CH_2)_{1-4}$-phenyl-, preferably for —$CH_2$-phenyl-,
Halogen stands for F, Cl, Br, or I.
Further definitions which will be used below are:
$C_2$-$C_{20}$alkenyl such as ethenyl (=vinyl), n-(=allyl), i-propenyl, n-but-(1-, 2-, or 3-)enyl, i-but(1- or 2-)enyl, sec.-but (1-, 2- or 3-)enyl, tert.-butenyl, n-pentenyl, n-hexenyl, n-heptenyl, n-octenyl, n-nonenyl, n-decenyl, n-undecenyl, n-dodecenyl, n-tridecenyl, n-tetradecenyl, n-pentadecenyl, n-hexydecenyl (=palmityl), n-heptydecenyl, n-octadecenyl (=oleyl), preferably vinyl, oleyl, palmityl, halogen-$C_1$-$C_{18}$alkyl such as chloro-, bromo- or iodo-$C_1$-$C_{18}$alkyl, wherein $C_1$-$C_{18}$alkyl has the above meaning, in particular preferred is iodo-n-propyl, amino-$C_1$-$C_{18}$alkyl such as aminomethyl, 2-aminoethyl, 3-amino-n-propyl, 4-amino-n-butyl, 5-amino-n-pentyl, 6-amino-n-hexyl, 7-amino-n-heptyl, 8-amino-n-octyl, 9-amino-n-nonyl, 10-amino-n-decyl, 11-amino-n-undecyl, 12-amino-n-dodecyl, 13-amino-n-tridecyl, 14-amino-n-tetradecyl, 15-amino-n-pentadecyl, 16-amino-n-hexydecyl, 17-amino-n-heptydecyl, 18-amino-n-octadecyl, preferably for amino-$C_1$-$C_4$alkyl such as for aminomethyl, 2-aminoethyl, 3-amino-n-propyl, 4-amino-n-butyl, more preferably for 3-amino-n-propyl, amino-$C_6$- or $C_{12}$aryl, such as aminophenyl, preferably o-, m-, or p-aminophenyl, more preferred p-aminophenyl, mercapto-$C_1$-$C_{18}$alkyl, mercaptomethyl, 2-mercaptoethyl, 3-mercapto-n-propyl, 4-mercapto-n-butyl, 5-mercapto-n-pentyl, 6-mercapto-n-hexyl, 7-mercapto-n-heptyl, 8-mercapto-n-octyl, 9-mercapto-n-nonyl, 10-mercapto-n-decyl, 11-mercapto-n-undecyl, 12-mercapto-n-dodecyl, 13-mercapto-n-tridecyl, 14-mercapto-n-tetradecyl, 15-mercapto-n-pentadecyl, 16-mercapto-n-hexydecyl, 17-mercapto-n-heptydecyl, 18-mercapto-n-octadecyl, preferably for mercapto-$C_1$-$C_4$alkyl such as for mercaptomethyl, 2-mercaptoethyl, 3-mercapto-n-propyl, 4-mercapto-n-butyl, more preferably 3-mercapto-n-propyl.

Compounds (1a') are known or can be prepared in analogy to known methods. E.g. the use of functional mono-, bis- and tris-alkoxysilanes for coupling and modification of co-reactive functional groups is described in Kirk-Othmer, Encyclopedia of Chemical Technology, Vol. 20, 3rd Ed., J. Wiley, N.Y.

In a preferred embodiment of this invention the co-reactive organo-silanes (1a') are aminosilanes (1a''), $R_1R_2R_3$Si-E-$NH_2$, in which E for stands for $C_1$-$C_{24}$alkylene, preferably $C_1$-$C_{18}$alkylene, more preferably $C_1$-$C_8$alkylene, or o-, m-, p-phenylene, and $R_1$=$R_2$=$R_3$ are —OH, $C_1$-$C_{18}$alkoxy or $C_1$-$C_{18}$alkoxy, which is substituted by $C_1$-$C_4$alkoxy. Particularly preferred are aminoalkyltrialkoxysilanes, i.e. in which E stands for $C_1$-$C_8$alkylene and $R_1$=$R_2$=$R_3$ are $C_1$-$C_4$alkoxy such as 3-amino-n-propyltrimethoxyilane and 3-amino-n-propyltriethoxysilane, most preferred is 3-amino-n-propyltriethoxysilane ("APTES").

Also preferred are amino-phenyl-tri-alkoxysilanes, in which E stands for o-, m-, p-phenylene, and $R_1$=$R_2$=$R_3$ are $C_1$-$C_8$alkoxy or with $C_1$-$C_4$alkoxy substituted $C_1$-$C_4$alkoxy, such as o-aminophenyl-, m-aminophenyl-, p-aminophenyl-trialkoxysilanes, preferably p-aminophenyl-trialkoxysilanes. In particular preferred are p-aminophenyl-trialkoxysilanes.

Also mixtures of aminoalkyltrialkoxysilanes and aminoaryltrialkoxysilanes can be used.

In case of compound (1a') is an isocyanoto-silane, 3-isocyanato-propyltriethoxysilane is most preferred.

In case of compounds (1a') is an isothiocyanoto-silane, 3-isothiocyanato-n-propyltriethoxysilane is most preferred.

In case of compound (1a') is a mercapto-silane, mercaptomethyl(methyl)diethoxysilane, 3-mercapto-n-propyltriethoxysilane, 3-mercapto-n-propyl(methyl)diethoxysilane, 3-mercapto-propyl-di-methyl-ethoxysilane are preferred, most preferred is 3-mercapto-n-propyltriethoxysilane.

In case compound (1a') is a halogenated organo-silanes, 3-iodo-n-propyl-triethoxysilane and 3-bromo-n-propyl-triethoxysilane are most preferred.

Although not desired to be limited by theory, the coupling usually arises as a result of hydrolysis of the alkoxysilane groups to silanol groups, see e.g. E. Pluedemann, Silane Coupling Agents, Plenum Press, N.Y. 1982.

In a preferred embodiment of this invention the functionalized dyestuff is prepared by the reaction of a co-reactive aminosilane (1a″) with a reactive dyestuff (D-hal):

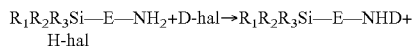

R₁R₂R₃Si—E—NH₂+D-hal→R₁R₂R₃Si—E—NHD+ H-hal

As reactive dyestuff D-hal the known dyestuffs can be used, preferably chemically reactive dyes as mentioned above are used. In particular preferred are naphthalimides, porphycenes, rhodamines, fluoresceines, stilbenes, xanthenes, and benzoxanthenes.

As co-reactive aminosilane $R_1R_2R_3Si\text{-}E\text{-}NH_2$ (1a″) those are preferred, where $R_1$, $R_2$, $R_3$ stand for —OH, $C_1$-$C_8$alkoxy, and E stands for $C_1$-$C_8$alkylene, $C_6$- or $C_{12}$aryl, or $(C_6\text{-})$ar $(C_{1-4})$alkylene.

Most preferred co-reactive aminosilanes $R_1R_2R_3Si$—E—$NH_2$ (1a″) such as 4-amino-n-butyltriethoxysilane, 3-amino-n-propyltriethoxysilane, 3-amino-n-propyltrimethoxysilane, 3-amino-n-propylsilanetriol, (3-amino-n-propyl)-methyl-dimethoxysilane, (3-amino-n-propyl)-di-methyl-methoxysilane, N-(2-aminoethyl)-3-amino-n-propyltrimethoxysilane, N-(2-aminoethyl)-3-amino-n-propylmethyldimethoxysilane, N-(6-aminohexyl)-3-amino-n-propyltrimethoxysilane, and amino-o-, -m-, -p-phenyltrimethoxysilanes as well as its isomer mixtures.

Generally, the reactive dyestuff D-hal is dissolved in a solvent and the co-reactive aminosilane (1a″) is added. After the addition, preferably the reaction is allowed to proceed to completion. Of course, the reaction also can be carried out using suspensions and the like.

Preferably, the molar ratio of aminosilane (1a″) to dyestuff D-hal is chosen in the range of 1:1 to 100:1, preferably from 2:1 to 15:1.

Preferred solvents are organic solvents, in particular polar solvents such as acetonitrile, alcohols like ethanol, methanol, 1-propanol, 2-propanol, 1-methoxy-2-propanol, tetrahydrofurane ("THF"), dioxane, pyridine, N-methylpyrrolidone ("NMP"), dimethylformamide ("DMF"), dimethylacetamide ("DMAA"), ketones like tert.-butylmethylketone, preferably ethanol, dimethylacetamide, dimethylformamide and acetonitrile. Of course, also mixtures of solvents can be used, too. Naturally, other solvents can be used as long as they do not interfere negatively with the reaction.

Generally, the reaction is carried out in a temperature range from −10° C. to the boiling point of the reaction mixture, which as a rule is in the range of the boiling point of the used solvent or solvent mixture.

For example, when carrying out the reaction in dimethylacetamide or pyridine the preferred temperature is in the range of 50 to 100° C., preferably in the range of 70 to 90° C. Or when, for example, the reaction is carried out in acetonitrile, the preferred temperature range is chosen between 40 to 80° C., more preferably from 50 to 75° C.

The duration of the addition of the aminosilane (1a″) as well as of the whole reaction depends on the reactivity of e.g. the chosen educts, amounts and temperature. Usually a person skilled in the art will know what to do and when the reaction is completed. A typical time range for the addition of the aminosilane (1a″) would be from 10 min to 2 hours, preferably from 10 to 60 min. A typical time range for completion of the reaction would be from 1 to 12 hours, preferably from 1 to 6 hours.

If desired the obtained product can be isolated by known methods such a filtration, centrifugation, crystallization, decantation, chromatography, evaporation/distillation of residual solvents and reactants and the like.

In another preferred embodiment of this invention the functionalized dyestuff is prepared by the reaction of the co-reactive aminosilane (1a″) with a reactive dyestuff comprising a lactone group

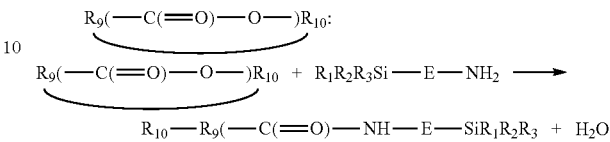

wherein $R_9$ and $R_{10}$ together with —C(=O)—O— form a lactone group within the dyestuff molecule.

In principle, all lactone group containing dyestuffs can be used, preferred are rhodamine and fluoresceine based compounds such as rhodamine B, fluoresceine and the like.

As co-reactive aminosilane (1a′) the abovementioned aminosilanes (1a″) are preferred.

Usually, this ring-opening reaction is carried out in the presence of an acid such as a mineral acid, e.g. HCl, and HBr, or dicyclohexylcarbodiimide ("DCC").

Generally, the reactive lactone dyestuff is dissolved in a solvent and the co-reactive aminosilane (1a″), is added. After the addition, preferably the reaction is allowed to proceed to completion. Of course, the reaction also can be carried out using suspensions and the like.

Preferably, the molar ratio of aminosilane (1a″) to dyestuff is chosen in the range of 1:1 to 100:1, preferably from 2:1 to 15:1.

Usually this reaction is carried out in the presence of a solvent. Preferred solvents are organic solvents such as polar solvents like acetonitrile, alcohols like ethanol, methanol, 1-propanol, 2-propanol, 1-methoxy-2-propanol, tetrahydrofurane ("THF"), dioxane, pyridine, N-methylpyrrolidone ("NMP"), dimethylformamide ("DMF"), dimethylacetamide ("DMAA"), ketones like tert.-butylmethylketone, preferably ethanol, 1-methoxy-2-propanol, dimethylacetamide, dimethylformamide and acetonitrile. Of course also mixtures of solvents can be used, too. Naturally, other solvents can be used as long as they do not interfere negatively with the reaction.

Generally, the reaction is carried out in a temperature range from 0° C. to the boiling point of the reaction mixture, which usually is in the range of the boiling point of the used solvent or solvent mixture.

For example when carrying out the reaction in dimethylacetamide or pyridine the preferred temperature is in the range of 0 to 100° C., preferably in the range of 0 to 60° C.

The duration of the addition of the aminosilane (1a″) as well as of the whole reaction depends on the reactivity of e.g. the chosen educts, amounts and temperature. Usually a person skilled in the art will know what to do and when the reaction is completed. A typical time range for the addition of the aminosilane (1a″) would be from 10 min to 2 hours, preferably from 10 to 60 min. A typical time range for completion of the reaction would be from 1 to 12 hours, preferably from 1 to 6 hours.

If desired the obtained product can be isolated by known methods such a filtration, centrifugation, crystallization, decantation, chromatography, evaporation/distillation of residual solvents and reactants etc.

In another preferred embodiment of this invention the functionalized dyestuff is prepared by the reaction of the co-reactive aminosilane (1a") with a reactive dyestuff comprising a isothiocyanate group D—N=C=S or an active ester like succinimidyl-ester:

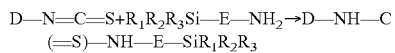

Such reactions are well-known in the art and e.g. a similar reaction is described in Langmuir, Vol. 8, No. 12, 1992, p. 2924).

Of course, it is also possible to use educts where the amino group comes with the dye and the isothiocyanato group comes with the silane.

As reactive dyestuff succinimidylesters and all isothiocyanato group containing dyestuffs can be used such as rhodamine derivatives, preferably tetraethylrhodamine-5/6-isothiocyanate (TRITC), fluoresceine-5-isothiocyanate (FITC), 7-dimethylamino-4-methylcoumarin-3-isothiocyanate (DACITC), eosin-5-isothiocyanate, erythrosin-5-isothiocyanate, malachite green isothiocyanate and the like.

Generally, the reactive dyestuff D—N=C=S or a corresponding succinimidylester is dissolved in a solvent and the co-reactive aminosilane (1a") is added. After the addition, preferably the reaction is allowed to proceed to completion. Of course, the reaction also can be carried out using suspensions and the like.

Preferably, the molar ratio of aminosilane (1a") to dyestuff is chosen in the range of 1:1 to 100:1, preferably from 2:1 to 15:1.

Usually this reaction is carried out in the presence of a solvent. Preferred solvents are organic solvents, in particular polar solvents such as acetonitrile, alcohols like ethanol, methanol, 1-propanol, 2-propanol, 1-methoxy-2-propanol, tetrahydrofurane ("THF"), dioxane, pyridine, N-methylpyrrolidone ("NMP"), dimethylformamide ("DMF"), dimethylacetamide ("DMAA"), ketones like tert.-butylmethylketone, preferably ethanol, 1-methoxy-2-propanol, dimethylacetamide, dimethylformamide and acetonitrile. Of course also mixtures of solvents can be used, too. Of course, other solvents can be used as long as they do not interfere negatively with the reaction. A person skilled in the art would know what to choose in such a case.

Generally, the reaction is carried out in a temperature range from 0° C. to the boiling point of the reaction mixture, which usually is in the range of the boiling point of the used solvent or solvent mixture.

For example, when carrying out the reaction in dimethylacetamide or pyridine the preferred temperature is in the range of 0 to 100° C., preferably in the range of 0 to 60° C.

The duration of the addition of the aminosilane (1a") as well as of the whole reaction depends on the reactivity of e.g. the chosen educts, amounts and temperature. Usually a person skilled in the art will know what to do and when the reaction is completed. A typical time range for the addition of the aminosilane (1a") would be from 10 min to 2 hours, preferably from 10 to 60 min. A typical time range for completion of the reaction would be from 1 to 48 hours, preferably from 1 to 24 hours.

If desired the obtained product can be isolated by known methods such a filtration, centrifugation, crystallization, decantation, chromatography, evaporation/distillation of residual solvents and reactants etc.

In another preferred embodiment of this invention the functionalized dyestuff can be prepared by the reaction of a co-reactive isocyanatosilane $R_1R_2R_3Si$—E—NCO with a reactive hydroxy- or amino-dyestuff D—$Z_1$, wherein $Z_1$ can be —OH or —$NH_2$:

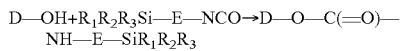

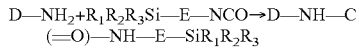

In cases where the hydroxyl group of the dyestuff is not stable, it is more appropriate to use a corresponding protective group, e.g. an ester like acetoxy. The hydroxyl group is usually then generated in situ or before the reaction with the isocyanatosilane for example by reaction of the ester with a common base such as a alkali metal alcoholate like sodium methylate.

As reactive ester-dyestuff, which is a precursor of the corresponding hydroxy-dyestuff D—OH, porphycenes such as 9-hydroxy-substituted 2,7,12,17-tetraalkyl-, -aryl-, -alkoxyalkyl- or -alkylaryl-, -alkoxyaryl-porphycenes and mixtures thereof like mono-, di-, tri-2,7,12,17-substituted porphycenes, 2,7,12,17-alkylarylsubstituted-3,6,13,16-tetraazaporphycenes, preferably 9-hydroxy-2,7,12,17-tetrakis(methoxyethyl)-porphycene, 9-hydroxy-2,7,12,17-tetra-n-propylporphycene can be used.

As reactive amino-dyestuff D—$NH_2$ porphycenes like 9-amino-substituted 2,7,12,17-tetraalkyl-, -aryl-, -alkoxyalkyl- or -alkylaryl-, -alkoxyaryl-porphycenes and mixed substituted porhycenes like mono-, di-, tri-2,7,12,17-substituted porphycenes, 2,7,12,17-alkylarylsubstituted-3,6,13,16-tetraazaporphycenes, preferably 9-amino-2,7,12,17-tetrakis(methoxyethyl)-porphycene, 9-amino-2,7,12,17-tetra-n-propylporphycene can be used.

As co-reactive isocyanatosilane $R_1R_2R_3Si$—E—NCO those silanes are preferred in which $R_1=R_2=R_3$ stand for $C_1$-$C_4$alkoxy such as methoxy, ethoxy, n-, i-propoxy, n-, sek.-, tert.-butoxy, preferably methoxy and ethoxy, and E stands for $C_1$-$C_8$alkylene such as methylene, ethylene, n-, i-propylene, n-, i-, sec.-, tert.-butylene, n-pentylene, n-hexylene, n-heptylene, n-octylene, particularly preferred $C_1$-$C_4$alkylene such as methylene, ethylene, n-, i-propylene, n-, i-, sec.-, tert.-butylene, most preferred for n-propylene. In particular preferred is 3-isocyanato-n-propyl-triethoxysilane.

Similar reactions are known, for example described in Chem. Phys. Letters 245 (1995) 36-40). Generally, the reactive dyestuff D—$Z_1$ is dissolved in a solvent and the co-reactive isocyanatosilane is added. After the addition, preferably the reaction is allowed to proceed to completion. Of course, the reaction also can be carried out using suspensions and the like.

Preferably, the molar ratio of isocyanatosilane $R_1R_2R_3Si$—E—NCO to dyestuff is chosen in the range of 1:1 to 100:1, preferably from 2:1 to 15:1.

Usually this reaction is carried out in the presence of a solvent. Preferred solvents are organic solvents such as polar solvents like acetonitrile, alcohols like ethanol, methanol, 1-propanol, 2-propanol, tetrahydrofurane ("THF"), dioxane, pyridine, N-methylpyrrolidone ("NMP"), dimethylformamide ("DMF"), dimethylacetamide ("DMAA"), ketones such as tert.-butylmethylketone, preferably ethanol, dimethylacetamide, dimethylformamide and acetonitrile. Of course, also mixtures of solvents can be used, too. Naturally, other solvents can be used as long as they do not interfere negatively with the reaction.

As a rule, the reaction can be carried out in a temperature range from 0° C. to the boiling point of the reaction mixture, which usually is in the range of the boiling point of the used solvent or solvent mixture.

For example, when carrying out the reaction in dioxane or THF the preferred temperature is in the range of 0 to 50° C., preferably in the range of 5 to 30° C.

The duration of the addition of the isocyanatosilane R₁R₂R₃Si—E—NCO as well as of the whole reaction depends on the reactivity of e.g. the chosen educts, amounts and temperature.

Usually a person skilled in the art will know what to do and when the reaction is completed. A typical time range for the addition of the isocyanatosilane R₁R₂R₃Si—E—NCO would be from 10 min to 2 hours, preferably from 10 to 60 min. A typical time range for completion of the reaction would be from 1 to 48 hours, preferably from 1 to 24 hours.

If desired the obtained product can be isolated by known methods such a filtration, centrifugation, crystallization, decantation, chromatography, evaporation/distillation of residual solvents and reactants and the like.

The spacer of the formula (1b)

$$R_{4(4-m)}SiX_m \quad (1b)$$

wherein each

R₄ represents a monovalent organic radical of from 1 to 24 carbon atoms, optionally substituted by a monovalent organic radical, X represents a group capable of undergoing hydrolysis and m is 0, 1, 2, 3 or 4, preferably 3;

are either well-known and commercially available (e.g. from Fluka, Aldrich or ABCR Gelest) or can be synthesized by well-known methods. In case more than one group R₄ is in the spacer molecule, then it can be the same or different, the same applies for the group X.

Examples of a monovalent organic radical of from 1 to 24 carbon atoms, optionally substituted by a monovalent organic radical, are $C_1$-$C_{24}$alkyl as defined above, $C_5$-$C_8$cycloalkyl such as cyclopentyl, cyclohexyl, cycloheptyl, cyclooctyl, preferably cyclohexyl, $C_2$-$C_{20}$alkenyl as defined above, preferably vinyl, oleyl, palmityl, halogen-$C_1$-$C_{18}$alkyl, amino-$C_1$-$C_{10}$alkyl, amino-$C_6$-$C_{12}$aryl, mercapto-$C_1$-$C_{18}$alkyl all as defined above.

Examples of a group capable of undergoing hydrolysis, X, are $C_1$-$C_8$alkoxy and $C_1$-$C_6$acyloxy (as in tri-acetoxy-methylsilane)

such as methoxy, ethoxy, n-, i-propoxy, n-, i-, sec.-, tert.-butoxy, n-pentoxy, n-hexoxy, n-heptoxy, n-octoxy, preferably for $C_1$-$C_4$alkoxy such as for methoxy, ethoxy, n-propoxy, n-butoxy, formyloxy, acetoxy, n-, i-propoyloxy, n-, i-, sec.-, tert.-butyloxy, n-pentoyloxy, n-hexoyloxy, preferably acetoxy.

In particular preferred spacers (1b) are n-$C_1$-$C_{18}$alkyl-tri ($C_1$-$C_8$alkoxy)silanes such as methyltrimethoxysilane, methyltriethoxysilane, ethyl-trimethoxysilane, ethyl-triethoxysilane, n-propyl-trimethoxysilan, n-propyl-triethoxysilan, n-butyl-trimethoxysilane, n-octyl-trimethoxysilane, n-octadecyl-trimethoxysilane, n-butyl-triethoxysilane, n-octyl-triethoxysilane, n-octadecyl-triethoxysilane.

Of course, also mixtures of spacers (1a) can be used. E.g. a preferred mixture can be chosen from methyltrimethoxysilane and n-propyltrimethoxysilane, wherein a preferred mixing range would be from 1:10 to 10:1, more preferably in the range of from 0.9:1 to 1.1:1.

Generally, the functionalized dyestuff (1a) is reacted with the silane spacer (1b), wherein the molar ratio of silane spacer (1b) to functionalized dyestuff (1a) is chosen in the range of from 1:10 to 100:1, preferably from 1:1 to 50:1.

The catalyst, which usually is an acid or a base, is added in order to start and maintain the reaction between the functionalized dyestuff (1a) and the spacer (1b).

As acid the usual mineral acids or simple organic acids can be used such as HCl, HF, CF₃COOH, ClH₂COOH, p-toluene sulfonic acid and the like.

As base the usual bases can be used such as alkali metal hydroxides like lithium hydroxide, sodium hydroxide or potassium hydroxide, earth alkali metal hydroxides such as magnesium hydroxide, calcium hydroxide, ammonium hydroxide, or alkali metal carbonates or earth alkali metal carbonates like sodium carbonate, potassium carbonate, magnesium carbonate, calcium carbonate or earth alkali metal hydrogen carbonates like calcium hydrogen carbonate.

Generally, the catalyst is added in aqueous form, e.g. in a preferred embodiment a 25% by weight aqueous ammonia solution is used.

The amount of catalyst to functionalized dyestuff (1a) usually is chosen in the range of from 10:1 to 1:20 mol.-%.

It can be advantageous to carry out this reaction in the presence of an appropriate solvent. Such solvents can easily be chosen by a person skilled in the art. As examples the following solvents can be used: water, alcohols such as methanol, ethanol, 1-propanol, 2-propanol, methoxyethanol, 1-methoxy-2-propanol, tetrahydrofurane, acetone, N,N-dimethyl acetamide, N-methylpyrrolidone ("NMP"), dioxane, tert.-butylmethylketone, or mixtures thereof. Usually the amount of solvent is chosen in the range of from 5 to 99.9% by weight, preferably from 30 to 99% by weight, based on the amount of functionalized dyestuff.

As a rule, the sequence of addition is not important for the success of the invention. Usually, a mixture of the functionalized dyestuff (1a), the spacer (1b) and a solvent is added to a mixture of the catalyst and a solvent or solvent mixture.

The time, when all three main components are combined is called $T_{SB}$.

The obtained reaction mixture is then treated until time $T_{SE}$, wherein the difference ($T_{SE}$–$T_{SB}$) usually is chosen in the range of from 1 and 48 hours.

Generally, the treatment is carried out at a temperature in the range of from 0 to 80, preferably 10 to 50° C.

After this first stage, it is possible to isolate the desired product, e.g. by known methods such as centrifugation, decantation, filtration or chromatography and the like. The obtained particles will be called silsesquioxanes below.

Preferably, though, the process is carried on by adding a co-reactive compound (1c), which is selected from the group consisting of an organic silane, an organic alumina, an organic zirconia and an organic titania.

Co-reactive compounds (1c) are known and commercially available or can be synthesized by known methods.

Preferred organic silanes are e.g. unsubstituted or substituted tetra-$C_1$-$C_8$alkoxysilanes such as tetramethoxysilane, tetraethoxysilane ("TEOS"), tetra-n-propoxysilane, tetra-n-butoxysilane; tetrakis(methoxyethoxy)silane, tetrakis (ethoxyethoxy)silane, tetrakis(methoxyethoxyethoxy)silane, tetrakis(methoxypropoxy)silane, tetrakis(2-methylhexoxy) silane, di-$C_1$-$C_4$alkyl-tetra-$C_1$-$C_8$alkoxydisilanes such as dimethyltetraethoxydisiloxane; tetra-$C_1$-$C_4$acyloxysilanes such as tetraacetoxysilane; tetra-$C_2$-$C_4$alkenyloxysilanes such as tetraallyloxysilane, as well as mixtures thereof, preferably tetraethoxysilane (TEOS) and tetra-n-propoxysilane.

As co-reactive organic alumina such as tri-$C_1$-$C_4$alkoxy aluminate like tri-n-, -i-propoxy aluminate, tri-n-butoxy aluminate, but also alkoxy alumina-silica compounds like di-$C_1$-$C_4$alkoxy aluminoxy tri-$C_1$-$C_4$alkoxy silanes such as di-butoxy-aluminoxy-triethoxy-silane, can be used.

As co-reactive organic zirconia such as tetra-$C_1$-$C_4$alkoxy zirconate like tetra-n-butoxy zirconate, tetraethoxy zirconate, tetra-n-, -i-propoxy zirconate, can be used.

As co-reactive organic titania such as tetra-$C_1$-$C_4$alkoxy titanate like tetra-n-butyl titanate, tetraethoxy titanate, tetramethoxy titanate, tetra-n-, -i-propoxy titanate, can be used.

The amount of silsesquioxane to the co-reactive compound (1c) is usually chosen in the range of from 0.1 to 99% by weight to 2 to 90% by weight.

The time of adding the co-reactive compound (1c) is called $T_{CC}$, wherein $T_{CC}$ fulfils condition (a) $T_{CC} \geq T_{SE}$,
(b) $T_{SB} < T_{CC} < T_{SE}$, or
(c) $T_{SB} < T_{CC1} < T_{SE} \leq T_{CC2}$ in case part of co-reactive compound (1c) is added before $T_{SE}$, and the other part after $T_{SE}$.

After the addition of the co-reactive organic compound (1c) the obtained reaction mixture is treated for a period of time between 1 and 48, preferably between 12 and 36 hours.

Usually the temperature is chosen in the range of 0 to 80, preferably from 10 to 50° C.

Preferably, the reaction is carried out in the presence of a solvent. In addition, it is preferred to add the co-reactive organic compound (1c) as a mixture with an appropriate solvent.

Such solvents can be e.g. polar solvents such as water, alcohols such as methanol, ethanol, 1-propanol, 2-propanol, methoxyethanol, methoxypropanol, ethers like dioxane, tetrahydrofurane, or N-containing solvents such as acetonitrile, N,N-di-methyl formamide, N,N-di-methyl acetamide, N-methylpyrrolidone or mixtures thereof. Usually the amount of solvent is chosen in the range of from 5 to 99.9% by weight, preferably from 30 to 99% by weight, based on the amount of functionalized dyestuff.

Furthermore, advantageously the reaction mixture is stirred, in particular vigorously during the addition of the co-reactive compound (1c).

The obtained reaction product can be separated from the reaction mixture by known methods such as centrifugation, decantation, filtration, or chromatography and the like.

As a rule, the separated product can be further treated and worked-up. A preferred method is to disperse the separated product in a solvent such as alcohol like ethanol, n-, i-propanol, methoxypropanol, or N,N-di-methyl formamide, N,N-di-methyl acetamide, tetrahydrofurane, dioxane, acetonitrile, N-methylpyrrolidone, preferably in ethanol or di-methyl acetamide, and then to precipitate the desired product by addition of another solvent such as ethyl acetate, butyl acetate, hexane, cyclohexane, toluene, preferably ethyl acetate.

After precipitation the desired product can be further washed in order to remove undesired starting material or by-products if required. E.g. it can be washed in a solvent such as ethyl acetate, butyl acetate, propanol, methoxypropanol, dichloromethane, cyclohexane, toluene or hexane, and separated from the solvent by known methods such as centrifugation, filtration, decantation, and chromatography. Remaining solvent can be removed by known methods such as drying preferably in an atmosphere of reduced pressure.

For further use, generally, the desired product can be dispersed in a solvent such as an alcohol like methanol, ethanol, propanol, methoxypropanol, or such as an ether like diethyl ether, tetrahydrofurane, dioxane, or an ester such as ethyl acetate, or N,N-di-methyl acetamide, acetonitrile, preferably ethanol or ethyl acetate, and stored.

Optionally, after isolating the thus obtained nanoparticles with well-known methods, the nanoparticles can be combined with a polymer or, a monomer or monomer mixture is polymerized in the presence of the nanoparticles.

In a preferred embodiment of this invention the whole amount of co-reactive compound (1c) is added once or in small portions within a short period of time, e.g. from 1 to 15 minutes, at time $T_{CC}$, such that condition (a) $T_{CC} \geq T_{SE}$ is fulfilled.

Naturally, the times $T_{CC}$ and $T_{SE}$ depend on the nature of the reaction conditions and the reactivity of the educts. E.g. in case of using a n-$C_1$-$C_{18}$alkyl-tri($C_1$-$C_{18}$alkoxy)silane as spacer (1b) and tetra-$C_1$-$C_8$alkoxysilanes as co-reactive compound (1c) $T_{SE}$ is in the range of 1 to 24 h after $T_{SB}$, which means $T_{CC}$ can be chosen in the range of 24 h and upwards like 24 to 48 h. In other cases a person skilled in the art would know what to do, because the reaction conditions and reactivities of the desired educts are known or can be easily figured out.

Therefore, in a particular preferred embodiment, spacer (1b) is a n-$C_1$-$C_{18}$alkyl-tri($C_1$-$C_{18}$alkoxy)silane such as n-propyltrimethoxysilane or a mixture of different a n-$C_1$-$C_{18}$alkyl-tri($C_1$-$C_{18}$alkoxy)silanes such as n-propyltrimethoxysilane and methyltrimethoxysilane, and the co-reactive organic compound (1c) is a tetra-$C_1$-$C_8$alkoxysilane such as TEOS, and $T_{SE}$ is chosen such that the difference ($T_{SE}$–$T_{SB}$) is in the range of 1 to 24 h, and $T_{CC}$ in the range of from 24 to 48 h, or 0 to 24 h after $T_{SE}$.

The inventive compounds obtained by such a process will be called silica- (or alumina-, zirconia- or titania-) core-shell nanoparticles.

In another preferred embodiment of this invention the addition of co-reactive compound (1c) is chosen such that the condition (b) $T_{SB} < T_{CC} < T_{SE}$ is fulfilled.

The difference to the manufacture of silica (or alumina-, zirconia- or titania-) core-shell nanoparticles described above is the point in time of the addition of the co-reactive organic compound (1c), which is added before all spacer has reacted:

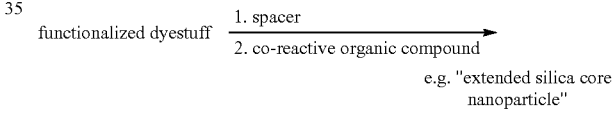

functionalized dyestuff $\xrightarrow{\text{1. spacer}}_{\text{2. co-reactive organic compound}}$ e.g. "extended silica core nanoparticle"

As stated above, the times $T_{CC}$ and $T_{SE}$ depend on the nature of the reaction conditions and the reactivity of the educts. E.g. in case of using a n-$C_1$-$C_{18}$alkyl-tri($C_1$-$C_{18}$alkoxy)silane as spacer (1b) and tetra-$C_1$-$C_8$alkoxysilanes as co-reactive compound (1c) $T_{SE}$ is in the range of 1 to 24 h after $T_{SB}$, which means $T_{CC}$ can be chosen in the range of 1 to 24 h after $T_{SB}$. In other cases a person skilled in the art would know what to do, because the reaction conditions and reactivities of the desired educts are known or can be easily figured out. Generally, after the addition of the co-reactive organic compound (1c) the reaction time is chosen in the range of from 1 to 48 hours, preferably from 12 to 36 h.

Therefore, in a particular preferred embodiment, spacer (1b) is a n-$C_1$-$C_{18}$alkyl-tri($C_1$-$C_{18}$alkoxy)silane such as n-propyltrimethoxysilane or a mixture of different a n-$C_1$-$C_{18}$alkyl-tri($C_1$-$C_{18}$alkoxy)silanes such as n-propyltrimethoxysilane and methyltrimethoxysilane, and the co-reactive organic compound (1c) is a tetra-$C_1$-$C_8$alkoxysilane such as TEOS, and $T_{SE}$ is chosen such that the difference ($T_{SE}$–$T_{SB}$) is in the range of 1 to 24 h, and $T_{CC}$ in the range of from 1 to 24 h, or 1 to 24 h after $T_{SE}$, preferably from 1 to 8 h after $T_{SE}$. Preferably, the reaction time is chosen between 12 and 36 h.

The inventive compounds obtained by such a process will be called extended silica- (or alumina-, zirconia- or titania-) core nanoparticles.

In another preferred embodiment of this invention the addition of co-reactive compound (1c) is split: part of the co-reactive compound (1c) is added before and the other part(s) after $T_{SE}$:

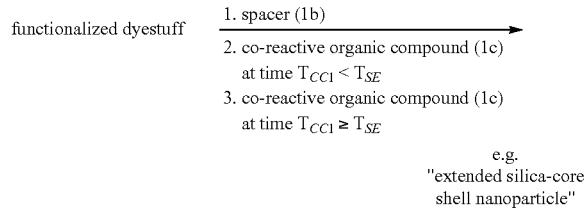

functionalized dyestuff
1. spacer (1b)
2. co-reactive organic compound (1c) at time $T_{CC1} < T_{SE}$
3. co-reactive organic compound (1c) at time $T_{CC1} \geq T_{SE}$ e.g. "extended silica-core shell nanoparticle"

In analogy to the above, the times $T_{CC1}$, $T_{CC2}$ and $T_{SE}$ depend on the nature of the reaction conditions and the reactivity of the educts. E.g. in case of using a n-$C_1$-$C_{18}$alkyl-tri($C_1$-$C_{18}$alkoxy)silane as spacer (1b) and tetra-$C_1$-$C_8$alkoxysilanes as co-reactive compound (1c) $T_{SE}$ is in the range of 1 to 24 h after $T_{SB}$, which means $T_{CC1}$ can be chosen in the range of 1 to 24 h after $T_{SB}$. In other cases a person skilled in the art would know what to do, because the reaction conditions and reactivities of the desired educts are known or can be easily figured out. Generally, after the first addition of a part or parts of the co-reactive organic compound (1c), i.e. before $T_{SE}$, i.e. at time $T_{CC1}$, the reaction is allowed to proceed in range of from 1 to 48 hours, preferably from 12 to 36 h, before the second or further addition(s) at time $T_{CC2}$ are made. In other words, the difference ($T_{CC2}-T_{CC1}$) preferably is chosen in the range of from 1 to 48, more preferably from 12 to 36 h. Usually, after each addition the reaction time is chosen in the range of from 1 to 48 hours, preferably from 12 to 36 h.

Therefore, in a particular preferred embodiment, spacer (1b) is a n-$C_1$-$C_{18}$alkyl-tri($C_1$-$C_{18}$alkoxy)silane such as n-propyltrimethoxysilane or a mixture of different a n-$C_1$-$C_{18}$alkyl-tri($C_1$-$C_{18}$alkoxy)silanes such as n-propyltrimethoxysilane and methyltrimethoxysilane, and the co-reactive organic compound (1c) is a tetra-$C_1$-$C_8$alkoxysilane such as TEOS, and $T_{SE}$ is chosen such that the difference ($T_{SE}-T_{SB}$) is in the range of 1 to 24 h. The first addition of the co-reactive organic compound (1c), preferably half of the required amount, is added at time $T_{CC1}$ in the range of from 1 to 24 h, or 1 to 24 h after $T_{SE}$, preferably from 1 to 8 h after $T_{SE}$. Then, preferably, the reaction time is chosen between 12 and 36 h. After that time the second portion is added and the reaction is allowed to proceed for another 12 to 36 h.

It is also possible to use different co-reactive compounds (1c) at different times $T_{CC1}$ and $T_{CC2}$, preferably the same co-reactive compound (1c) is used.

The inventive compounds obtained by such a process will be called extended silica- (or alumina-, zirconia- or titania-) core-shell nanoparticles.

In a further embodiment of the present invention the inventive nano-sized particles can be encapsulated by a polymer. This can be done by combining the nanoparticles with a polymer or by polymerizing a monomer or monomer mixture in the presence of the nanoparticles.

According to present results, the polymer can improve stability against oxygen and enhance fluorescence and light fastness. In addition, the polymer can act as a dispersant.

As polymer the following can be used: polyacrylonitril, polyacrylate, polymethacrylate, polymethylmethacrylate, polymethylacrylate, polyethylene, polystyrene, polypropylene and the like, or mixtures thereof, preferably polyacrylonitril, polyethylene, polymethylmethacrylate, or mixtures thereof.

Preferably, the polymers are transparent and/or crystalline.

Usually, the polymers have a low to medium ranged molecular weight, i.e. from e.g. 10,000 to 500,000 g/mol, e.g. a polyacrylonitril having a $T_g$ of 85° C. and a molecular weight of 150,000 g/mol, or a HDPE wax having a $T_g$ of 90° C.

Such polymers are well-known and usually commercially available. Usually the polymers or of course including copolymers are manufactured from monomers like acrylic acid, methacrylic acid, and its esters like e.g. methyl methacrylate, styrene, divinyl-benzene, acrylonitrile and the like as well as its mixtures.

As one embodiment of the invention related to polymers which are manufactured in the presence of the nanoparticles, of course the corresponding desired monomers are used. The preferred polymerization would be an emulsion polymerization, which is described below.

Usually, the ratio of polymer to nanoparticles is chosen in the range of from 1 to 99% by weight, preferably from 20 to 70% by weight, based on the weight of the nanoparticles.

Generally, a dispersion of the inventive nanoparticles and the desired polymer in a solvent, preferably a polar organic solvent such as dimethylsulfoxid, dimethylformamid (DMF), dimethylacetamide (DMA), N-methyl-pyrrolidone (NMP), acetonitril, ethanol, n-propanol, dimethylsulfoxid (DMSO) and the like, is treated under elevated temperature, typically in the range of from 20 to 120° C., preferably from 50 to 90° C. for a period of time preferably in the range of from 0.1 to 6 h. Then an additional solvent, also preferably a polar solvent such as water or an organic solvent or mixtures thereof like alcohols like methanol, ethanol, n-, propanol is added in order to precipitate the polymer.

The precipitation of the polymer is typically carried out in the range of from 20 to 120° C., preferably from 50 to 90° C. for a period of time in the range of usually from 0.1 to 3 h. Generally, the treatment is continued thereafter at preferably a temperature in the range of e.g. from 30 to 80° C. for preferably 1 to 10 hours. Afterwards the obtained solid product is separated by known methods such as filtration preferably at room temperature, and as a rule washed and dried, e.g. for 3 to 12 hours at a temperature of from 50 to 90° C. under an atmosphere of reduced pressure such as from 50 to 80 hPa.

Of course, there are other possibilities to initiate the precipitation of the polymer, e.g. by omitting the second solvent, but decreasing the temperature of the mixture accordingly or by evaporation of the solvent or parts thereof in such a way, that a precipitation occurs. Such methods are well known to the person skilled in the art, therefore no further explanations are necessary.

Another embodiment of this invention concerns a process of encapsulation of the nanoparticles by in-situ polymerization of monomers like acrylate, methacrylate, styrene, etc., and mixtures thereof, usually catalysed by known compounds in the art as AIBN, acids, bases, etc. or by the use of temperature induced polymerization techniques. The polymerization, preferably emulsion polymerization, as such is well-known for the person skilled in the art, e.g. from Handbook of Polymer Synthesis 1992, Hans Rytger Kricheldorf (ISBN 0824785150).

In a preferred embodiment of this invention, silica core-shell nanoparticles or the silsesquioxane compounds are encapsulated by the polymerization of methyl methacrylate in the presence of said silica core-shell nanoparticles.

Typically, a mixture of methyl methacrylate, azo-bisisobutyronitrile (AIBN) and a solvent is added to a dispersion or suspension of silica core-shell nanoparticles or silsesquioxanes in an aqueous solvent mixture and heated to start and maintain the polymerization reaction. After the end of polymerization, the reaction mixture is worked up in a usual way, such as separation of the desired product, washing and drying it. In some cases it is preferred to carry out the reaction under an inert atmosphere.

As an example, the solvent used for the silica core-shell nanoparticles suspension can be an alcohol, preferably a water-soluble alcohol such as methanol or ethanol, preferably a water-ethanol mixture.

The weight ratio of silica core-shell nanoparticles to solvent can be chosen in the range of from 1:10 to 1:200, preferably from 1:50 to 1:100. In can be advantageous to homogenize this mixture with known methods such as stirring or treating with ultrasonic waves.

Furthermore, the suspension obtained preferably is saturated with an inert gas like nitrogen or argon.

The solvent used in the methyl methacrylate mixture can be an alcohol, preferably a water-soluble alcohol such as methanol or ethanol.

The weight ratio of methyl methacrylate to solvent can be chosen in the range of from 1:1 to 100:1, preferably from 1:1 to 1:10. Furthermore, the solution obtained preferably is saturated with an inert gas like nitrogen or argon.

The weight ratio of methyl methacrylate to AIBN usually is chosen in the range of from 10:1 to 1000:1, and the weight ratio of methyl methacrylate to solvent preferably is chosen in the range of from 1:1 to 100:1, preferably 1:1 to 10:1.

The reaction temperature as a rule is chosen in the range of from 20 to 100°, preferably from 40 to 70° C.

The reaction time can be chosen in the range of from 12 h to 48 h, preferably from 18 to 36 h.

Another embodiment of this invention concerns a process for the manufacture of functionalized nanoparticles comprising the steps of:

a) combining a functionalized dyestuff of the formula (1a)

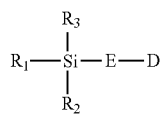

(1a)

wherein
$R_1$ stands for $C_1$-$C_{18}$alkoxy, —OH;
$R_2$, $R_3$ independently from each other stand for $C_1$-$C_{18}$alkoxy or $C_1$-$C_{18}$alkyl, —OH,
E stands for a direct bond or a bridging member,
D is the residue of a chromophore,
and a spacer of the formula (1b)

(1b)

wherein each
$R_4$ represents a monovalent organic radical of from 1 to 24 carbon atoms, optionally substituted by a monovalent organic radical,
X represents a group capable of undergoing hydrolysis and m is 0, 1, 2, 3 or 4;
a catalyst,
and optionally a solvent, at time $T_{SB}$,
and treating the obtained mixture until time $T_{SE}$, wherein ($T_{SE}$-$T_{SB}$) is chosen in the range of from 1 and 48 hours, at a temperature in the range of from 0 to 80° C., b) adding a co-reactive compound (1c) selected from the group consisting of an organic silane, an organic alumina, an organic zirconia and an organic titania, at time $T_{CC}$, wherein $T_{CC}$ fulfils condition (a) $T_{SB} < T_{CC} < T_{SE}$, (b) $T_{CC} \geq T_{SE}$ or (c) both (a) and (b) in case part of co-reactive compound (1c) is added before $T_{SE}$, and the other part after $T_{SE}$, and treating the obtained respective reaction mixture for a period of time between 12 and 36 hours at a temperature between 0 and 80° C., and, optionally, after isolating the thus obtained nanoparticles with well-known methods, c) combining the nanoparticles with a polymer or, d) polymerizing a monomer or monomer mixture in the presence of the nanoparticles.

The details for carrying out this process are already described above.

If desired the obtained treated silica core-shell nanoparticles and silsesquioxanes can be powdered by known methods such as milling, e.g. milling of the product, which has been cooled down well below the freezing point of water, e.g. with liquid nitrogen.

A further embodiment of this invention concerns the use of the inventive functionalized nanoparticles for coloring an organic material.

Still another embodiment of this invention concerns a composition comprising the inventive functionalized nanoparticles and an organic material.

The inventive nanoparticles can be used in all areas, where colored particles, in particular fluorescent particles can be applied such as in the fields of decoration, security, packaging, light managing energy collector systems (solar technology) and electronic materials, where colored polymer are applied, preferably with the additional condition, that the dyestuff does not exhibit any migration, for inks for ink jet, offset printing ink, for fluorescent coating paints, for medicinal diagnostic applications, for cosmetics (hair-dyeing, make-up, and the like), for color filters (polymer/paint formulation for displays, electronic applications), for electrophoretic color filter (e-paper), or for optical brighteners (for textile, paper, coatings, cosmetics).

The inventive nanoparticles exhibit improved quantum efficiency, an excellent migration stability, and an excellent thermostability.

EXAMPLES

Example 1

(a) Preparation of the Dyestuff 10.0 g of a commercial grade 4-chloronaphthalic anhydride (0.04 mol, tech. dried, from ACROS) is suspended in 50 ml of methanol at room temperature. A solution of 5.3 ml of isopentylamine (0.045 mol, Fluka purum 98%) in 10 ml methanol is added dropwise. The reaction mixture is heated to 65° C. and stirred overnight. The beige suspension is then filtered, washed with methanol and dried in a vacuum oven at 80° C. overnight.

(b) Functionalizing the Dyestuff 4.5 g (0.015 mol) of the above obtained dyestuff is dissolved in 10 ml of dimethylacetamide ("DMA"; Fluka purum) at 80° C. Then 33.2 g of 3-aminopropyltriethoxysilane (0.15 mol Aldrich) is added over a period of 30 min. After 2 h, the obtained orange solution is cooled to room temperature. Part of the product is isolated from the reaction mixture by chromatography with silica gel (X 60, Merck) and a solvent mixture of 10% of water, 40% of ethanol, 20% of pyridine and 30% ethyl acetate. The product is then isolated by evaporating the solvent as a brown paste.

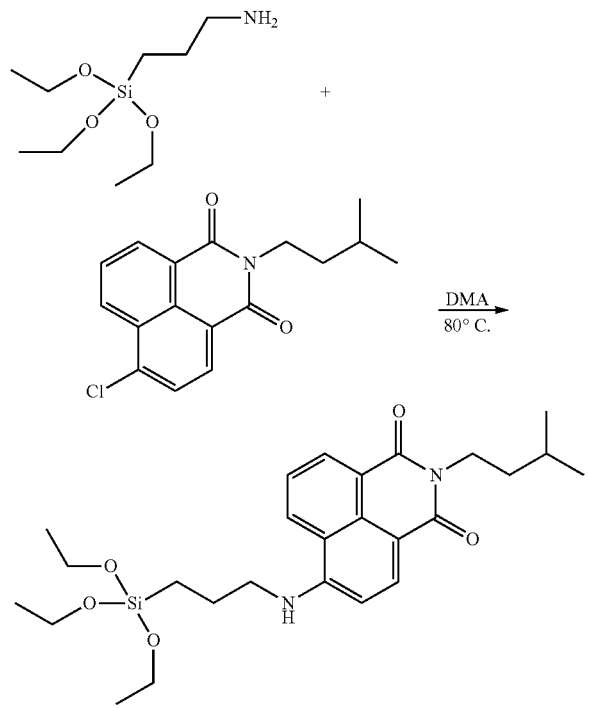

Example 1a

Reaction of Functionalized Dye with a Spacer; Silica Core-Shell Particles

A mixture of 0.25 g of the modified compound of example 1 as described above, 100 ml of 2-propanol and 2.5 g of n-propyltrimethoxysilane is added to a mixture of 150 ml of 2-propanol, 100 ml of deionized water and 30 g of 25% by weight aqueous ammonia solution (Fluka). The combined mixtures are stirred vigorously for 24 h at room temperature. Then, 5 g of tetraethoxysilane in 50 ml of 2-propanol are added. Afterwards this reaction mixture is stirred for 24 h and then centrifuged. The residue is dispersed in ethyl acetate, washed and centrifuged thrice, thereafter no starting material is found in the supernatant. The thus obtained residue is dried 24 h under an atmosphere of reduced pressure (70 hPa) at a temperature of 60° C.

Example 1aa

Synthesis of Extended Silica-Core-Particles

A mixture of 0.25 g of the modified dyestuff of example 1 as described above, 100 ml of 2-propanol and 2.5 g of n-propyltrimethoxysilane is added to a mixture of 150 ml of 2-propanol, 100 ml of deionized water and 30 g of 25% by weight aqueous ammonia solution (Fluka). The combined mixtures are stirred vigorously for 4 h at room temperature. Then, 5 g of tetraethoxysilane in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C.

Example 1aaa

Extended Silica-Core-Shell Particles

A mixture of 0.25 g of the modified dyestuff of example 1 as described above, 100 ml of 2-propanol and 2.5 g of n-propyltrimethoxysilane is added to a mixture of 150 ml of 2-propanol, 100 ml of deionized water and 30 g of 25% by weight aqueous ammonia solution (Fluka). The combined mixtures are stirred vigorously for 4 h at room temperature. Then, 2.5 g of tetraethoxysilane dissolved in 20 ml of ethanol is added to the vigorously stirred solution. The mixture is stirred for additional 24 h at room temperature, then another 2.5 g of tetraethoxysilane dissolved in 20 ml of ethanol is added to the vigorously stirred solution. The mixture is stirred for additional 24 h at room temperature. Thereafter, the thus obtained silica extended core-shell particles are separated from the reaction mixture by centrifugation. The separated extended core-shell particles are dispersed in ethanol, precipitated by addition of ethyl acetate, washed and centrifuged thrice until no starting material is found in the supernatant. The thus obtained residue is dried 24 h under an atmosphere of reduced pressure (70 hPa) at a temperature of 60° C. For storage, parts of the obtained residue are re-dispersed in ethanol.

The thus obtained residue is dried 24 h under an atmosphere of reduced pressure (70 hPa) at a temperature of 60° C.

Example 1b

Reaction of Functionalized Dye with a Mixture of Spacers; Silica-Core-Shell Particles A mixture of 0.25 g of the modified compound of example 1 as described above, 100 ml of 2-propanol, 1.25 g of n-propyltrimethoxysilane and 1.25 g of methyltrimethoxysilane is added to a mixture of 150 ml of 2-propanol, 100 ml of deionized water and 30 g of 25% by weight aqueous ammonia solution. The combined mixtures are stirred vigorously for 24 h at room temperature. Then, 5 g of tetraethoxysilane in 50 ml of 2-propanol are added. Afterwards this reaction mixture is stirred for 24 h and then centrifuged. The residue is dispersed in ethyl acetate, washed and centrifuged thrice, thereafter no starting material is found in the supernatant. The thus obtained residue is dried 24 h under an atmosphere of reduced pressure (70 hPa) at a temperature of 60° C.

Example 1bb

Extended Silica-Core-Particles

A mixture of 0.25 g of the modified dyestuff of example 1 as described above, 100 ml of 2-propanol, 1.25 g of n-propyltrimethoxysilane and 1.25 g of methyltrimethoxysilane is added to a mixture of 150 ml of 2-propanol, 100 ml of deionized water and 30 g of 25% by weight aqueous ammonia solution. The combined mixtures are stirred vigorously for 4 h at room temperature. Then, 5 g of tetraethoxysilane (Aldrich, 99.99%) in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C. Part of the obtained residue is stored as dispersion in ethanol.

Example 1bbb

Extended Silica-Core-Shell Particles

A mixture of 0.25 g of the modified dyestuff of example 1 as described above, 100 ml of 2-propanol, 1.25 g of n-propyltrimethoxysilane and 1.25 g of methyltrimethoxysilane is added to a mixture of 150 ml of 2-propanol, 100 ml of deionized water and 30 g of 25% by weight aqueous ammonia solution. The combined mixtures are stirred vigorously for 4 h at room temperature. Then, 2.5 g of tetraethoxysilane dissolved in 20 ml of ethanol is added to the vigorously stirred solution. The mixture is stirred for additional 24 h at room temperature, then another 2.5 g of tetraethoxysilane dissolved in 20 ml of ethanol is added to the vigorously stirred solution. The mixture is stirred for additional 24 h at room temperature. Thereafter, the thus obtained silica extended core-shell particles are separated from the reaction mixture by centrifugation. The separated extended core-shell particles are dispersed in ethanol, precipitated by addition of ethyl acetate, washed and centrifuged thrice until no starting material is found in the supernatant. The thus obtained residue is dried 24 h under an atmosphere of reduced pressure (70 hPa) at a temperature of 60° C. For storage, parts of the obtained residue are re-dispersed in ethanol.

The thus obtained residue is dried 24 h under an atmosphere of reduced pressure (70 hPa) at a temperature of 60° C.

Example 1c

Polymer (PAN) Encapsulated Silica Core-Shell Particles

A dispersion of 1 g of silica core-shell nano-particles of example 1a (see above) and 1.5 g of polyacrylonitrile (PAN, powder, Tg. 85° C., Tm. 317° C., Sigma-Aldrich) in 40 ml of DMSO is heated to 80° C. under vigorously stirring. After 2 h, 100 ml of 70% ethanol are added dropwise to the reaction mixture followed by an additional stirring for 8 h at a temperature of 50° C. Afterwards, the reaction mixture is filtered off, washed with 50 vol.-% of a ethanol/water mixture and dried for 24 h under an atmosphere under an atmosphere of reduced pressure (70 hPa) at a temperature of 60° C.

Example 1d

Polymer (PMMA) Encapsulated Silica Core-Shell Particles

A dispersion of 1.5 g of silica core-shell nano-particles of example 1a in 60 ml of ethanol and 5 g of water is saturated with nitrogen gas, and then treated with ultra sonic for 20 min for homogenization. The suspension is further treated with nitrogen gas under vigorously stirring at room temperature. 2 g of methyl methacrylate (MMA, Fluka) and 60 mg of azo-isobutyronitrile (AIBN, Aldrich) are dissolved in 1 g of ethanol and added to the suspension. After stirring the suspension under nitrogen for 24 h at a temperature of 50° C., the reaction mixture is cooled to room temperature, treated with ultra sonic for 20 min and centrifuged. The residue is washed two times with ethanol and dried in a vacuum oven under an atmosphere of reduced pressure (70 hPa) at a temperature of 60° C. (yield: 0.88 g). The polymer coated particles are treated with liquid nitrogen and milled in a mortar to obtain a fine powder.

0.4 g of the obtained product and 26.6 g of PVC (EVIPOL®SH 7020, EVC GmbH, Frankfurt/Main), 14.6 g of a stabilizing mixture consisting of 92.21% of a softening agent (diisodecyl phthalate, DIDP, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the used product. A migration test (according to DIN 53775 part 3: measured during 24 h at 80° C. and a pressure of 1 kg/cm², with heat stress during 30 min at 180° C.) is carried out: no migration could be observed, but a high fluorescence.

Comparative Example 1

Silica-Core-Shell Particles Without Spacer

A mixture of 0.25 g of the modified compound of example 1 as described above and 100 ml of 2-propanol (Merck, 98%) is added to a mixture of 150 ml of 2-propanol, 100 ml of deionized water and 30 g of 25% by weight aqueous ammonia solution. The combined mixtures are stirred vigorously for 24 h at room temperature. Then, 5 g of tetraethoxysilane in 50 ml of 2-propanol are added. Afterwards this reaction mixture is stirred for 24 h and then centrifuged. The residue is dispersed in ethyl acetate, washed and centrifuged thrice, thereafter no starting material is found in the supernatant. The thus obtained residue is dried 24 h under an atmosphere of reduced pressure (70 hPa) at a temperature of 60° C.

Comparative Example 2

Comparative Example "Surface Modification"

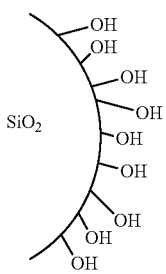

Ludox TMA

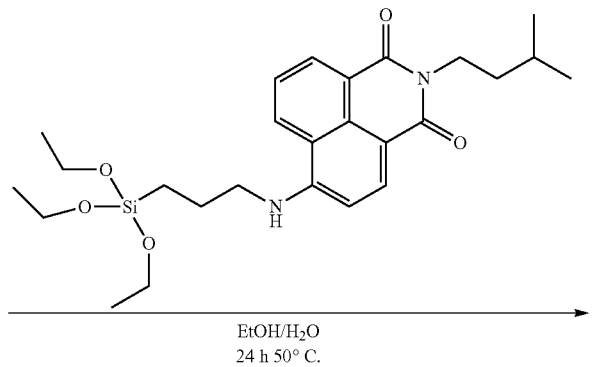

EtOH/H₂O
24 h 50° C.

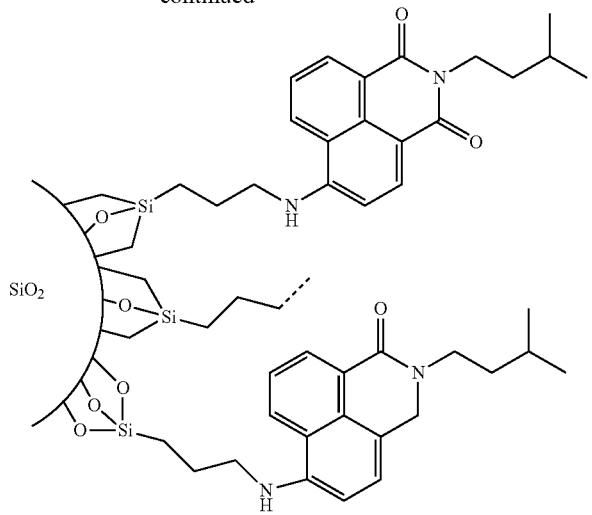

0.25 g of the fluorescent naphthalimide derivative as described above in example 1 are added to a suspension of 3 g nano-sized silica particles (34% $SiO_2$ in aqueous suspension, Ludox®TMA, RTM Aldrich) in 96% ethanol and heated 24 h at a temperature of 50° C. under vigorously stirring. After completion of the reaction and cooling down to room temperature, 50 ml of ethyl acetate are added to precipitate the fluorescent silica nanoparticles. The obtained suspension is centrifuged at 2000 rpm and washed with ethyl acetate until the supernatant is completely discoloured. The solid residue is then dried for 24 h under an atmosphere of reduced pressure (70 hPa) at a temperature of 60° C.

APPLICATION EXAMPLES

The nanoparticles of the above examples are checked in a PVC-foil application to compare fluorescence intensities and coloration abilities. The absorption of the samples are corrected to obtain the relative fluorescence quantum yield.

(A) Comparison of Photophysical Properties

The standard (comparative example 2) consists of surface modified silica nanoparticles, linked with fluorescence dye naphthalimide as described above. Comparative example 1, a core-shell nanoparticle without any spacer, is used as closest prior art example. All inventive examples 1a and 1b exhibit a higher relative fluorescence quantum yield ("FQY") compared to the comparative examples:

| Sample in PVC foil (0.5 mm) | FQY |
|---|---|
| surface modified sample (comp. ex. 2) | 1.00 |
| comparative example 1 | 0.38 |
| example 1a | 1.08 |
| example 1b | 1.29 |

Measurement of Fluorescence Quantum Yield in PVC Relative to Reference

Instrument: Cary Eclipse

| Sample Description | comp. ex. 1 | ex. 1a | Ex. 1b | (Reference) comp. ex. 2 |
|---|---|---|---|---|
| Matrix | PVC | PVC | PVC | PVC |
| Excitation wavelength [nm] | 440.0 | 440.0 | 440.0 | 440.0 |
| Excitation slit [nm] | 2.5 | 2.5 | 2.5 | 2.5 |
| Emission slit [nm] | 2.5 | 2.5 | 2.5 | 2.5 |
| Scan rate [nm/min] | 600.0 | 600.0 | 600.0 | 600.0 |
| Data interval [nm] | 1.0 | 1.0 | 1.0 | 1.0 |
| Averaging time [s] | 0.1 | 0.1 | 0.1 | 0.1 |
| Excitation filter | Auto | Auto | Auto | Auto |
| Emission filter | 360-1100 nm | 360-1100 nm | 360-1100 nm | 360-1100 nm |
| PMT voltage [V] | 810 | 810 | 810 | 810 |
| Relative Quantum Yield | 0.38 | 1.08 | 1.29 | 1.00 |

(B) Migration Resistance 0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed no migration:

| Sample 1% in PVC foil (0.5 mm) | Migration (Grey Scale) |
|---|---|
| Example 1a | 5 |
| Example 1aa | 5 |
| Example 1b | 5 |
| Example 1bb | 5 |

Migration scale from 1 to 5: wherein 5 = very good, no migration; 1 = bad (C) Heat Resistance Polyethylene (HDPE SABIC®M 80063S Powder) and 0.25% by weight, based on the total amount of polyethylene and sample, of a sample of the inventive product are extruded at a temperature of 300° C. So obtained chips with thickness of 2 mm are measured in a colorimeter in order to obtain the coloristic changes influenced by high temperature extrusion in HDPE:

| Sample HDPE (2 mm) 0.25% | DE |
|---|---|
| Example 1a | 0.8 |
| Example 1aa | 1.8 |
| Example 1b | 1.6 |
| Example 1bb | 1.2 |

Wherein DE expresses the deviation from hue, chroma and lightness. DE=0 means no color deviation at all. DE values below 2 are very good values and expected in industry.

Example 2

(a) Preparation of a Fluorescent Perinone (Step 1)

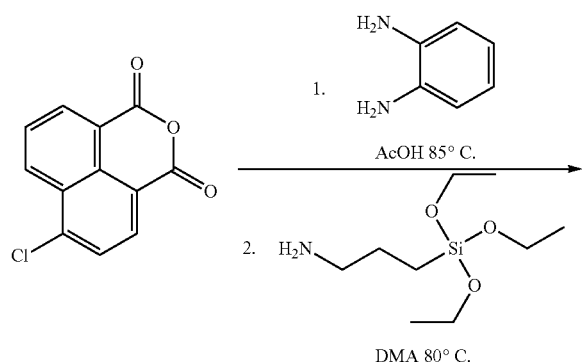

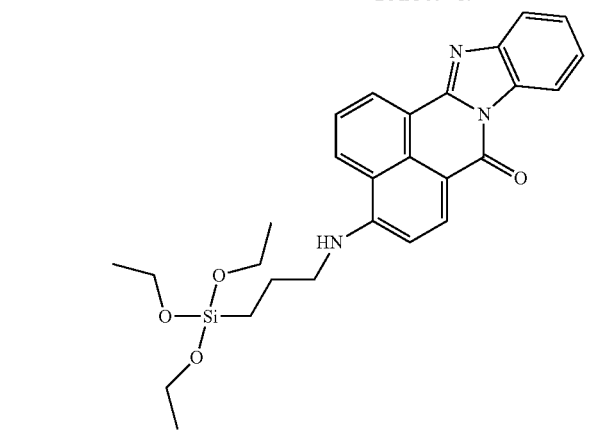

A mixture of 12.2 g of a commercial grade 4-chloronaphthalanhydride (0.05 mol, Acros tech. dried), 50 ml of acetic acid and 5.4 g of o-phenylendiamine (0.05 mol, Fluka purum 99%) is heated to 85° C. After 2 h the reaction mixture is cooled to room temperature followed by the addition of 200 ml of acetic acid. The obtained yellow suspension is then filtered, washed with acetic acid and water and dried in a vacuum oven at 80° C. overnight.

(b) Functionalizing the Dyestuff (Step 2)

4.6 g (0.015 mol) of the above perinone are suspended in 30 ml of dimethylacetamide at 80° C. Subsequently 33.2 g of 3-aminopropyltriethoxysilane ("APTES") (0.15 mol) are added over 15 min yielding a color change from yellow to orange after the end of addition. After 6 h the reaction mixture is cooled to room temperature. The desired product is obtained by chromatography (silica gel, eluent: ethyl acetate/toluene/pyridine 3:9:1), and subsequent work-up by evaporation of the solvent mixture.

Example 2a

Silica-Core-Shell Particles

A mixture of 0.25 g of the modified perinone of example 2 as described above, 100 ml of 2-propanol and 5 g of n-propyltrimethoxysilane is added to a mixture of 200 ml of 2-propanol, 150 ml of deionized water and 30 g of 25% by weight aqueous ammonia solution. The combined mixtures are stirred vigorously for 24 h at room temperature. Then, 5 g of tetraethoxysilane in 50 ml of 2-propanol are added. Afterwards this reaction mixture is stirred for an additional 24 h and then centrifuged. The residue is dispersed in ethyl acetate, washed and centrifuged thrice, thereafter no starting material is found in the supernatant. The thus obtained residue is dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2aa

Extended Silica-Core-Particles

A mixture of 0.25 g of the modified perinone of example 2 as described above, 100 ml of 2-propanol and 5 g of n-propyltrimethoxysilane is added to a mixture of 200 ml of 2-propanol, 150 ml of deionized water and 30 g of 25% by weight aqueous ammonia solution. The combined mixtures are stirred vigorously for 4 h at room temperature. Then, 5 g of tetraethoxysilane (Aldrich, 99.99%) in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C. For storage, parts of the above obtained product are re-dispersed in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 4.8).

Example 2b

Reaction of Functionalized Perinone with a Mixture of Spacers; Silica-Core-Shell Particles A mixture of 0.25 g of the modified perinone of example 2 as described above, 100 ml of 2-propanol, 2.5 g of n-propyltrimethoxysilane and 2.5 g of methyltrimethoxysilane is added to a mixture of 200 ml of 2-propanol, 150 ml of deionized water and 30 g of 25% by weight aqueous ammonia solution. The combined mixtures are stirred vigorously for 24 h at room temperature. Then, 5 g of tetraethoxysilane in 50 ml of 2-propanol are added. Afterwards this reaction mixture is stirred for 24 h and then centrifuged. The residue is dispersed in ethyl acetate, washed and centrifuged thrice, thereafter no starting material is found in the supernatant. The thus obtained residue is dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2bb

Extended Silica-Core-Particles

A mixture of 0.25 g of the modified perinone of example 2 as described above, 100 ml of 2-propanol, 2.5 g of n-propyltrimethoxysilane and 2.5 g of methyltrimethoxysilane is added to a mixture of 200 ml of 2-propanol, 150 ml of deionized water and 30 g of 25% by weight aqueous ammonia solution. The combined mixtures are stirred vigorously for 4 h at room temperature. Then, 5 g of tetraethoxysilane (Aldrich, 99.99%) in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2c

Silica-Core-Shell Particles; Perylene-bis-Imide-Silane Silica-Nanoparticles

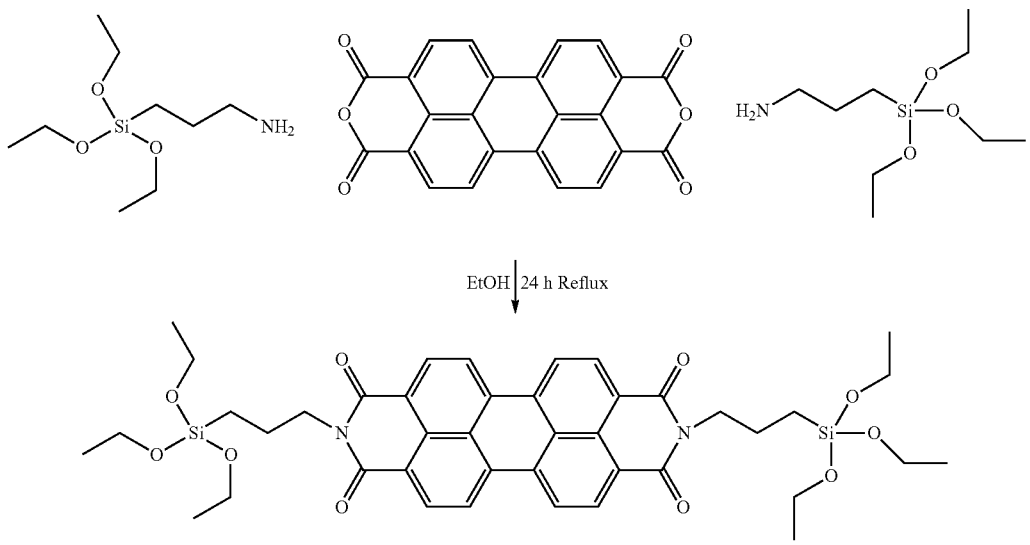

(a) Functionalizing a perylene derivative (see: *Chem. Mater.* 2000, 12, 352-362 M. Schneider, K. Muellen)

A mixture of 0.785 g (2 mmol) of 3,4:9,10-perylenetetracarboxylic bisanhydride and 70 ml of dry ethanol is stirred for ½ h under an argon atmosphere, then it is heated to 110° C. Thereafter, 3.542 g (16 mmol) of (3-aminopropyl)triethoxysilane (APTES) are added dropwise. The reaction mixture is stirred for 12 h at reflux conditions and under an inert atmosphere. After the mixture is cooled to room temperature, the precipitate is collected by suction filtration and washed thoroughly with cold ethanol. A dark red product is obtained in 82% yield.

(b) A mixture of 0.25 g of the modified perylene derivative obtained above, 80 ml of dimethylacetamide ("DMA"), 100 ml of 2-propanol and 5 g of n-propyltrimethoxysilane is added to a mixture of 200 ml of 2-propanol, 150 ml of deionized water and 30 g of 25% by weight aqueous ammonia solution. The combined mixtures are stirred vigorously for 24 h at room temperature. Then 5 g of tetraethoxysilane in 50 ml of 2-propanol are added. Afterwards this reaction mixture is stirred for additional 24 h and then centrifuged. The residue is dispersed in ethyl acetate, washed and centrifuged thrice until no starting material is found in the supernatant. The thus obtained residue is dried during 24 h in an atmosphere under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2cc

Extended Silica-Core-Particles

A mixture of 0.25 g of the modified perylene of example 2c as described above, combined first with 80 ml of DMA, 100 ml of 2-propanol and 5 g of n-propyltrimethoxysilane is added to a mixture of 200 ml of 2-propanol, 150 ml of deionized water and 30 g of 25% by weight aqueous ammonia solution. The combined mixtures are stirred vigorously for 4 h at room temperature. Then 5 g of tetraethoxysilane (Aldrich, 99.99%) in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2d

Silica-Core-Shell Particles

A mixture of 0.25 g of the modified perylene of example 2c as described above, combined first with 80 ml of DMA, 100 ml of 2-propanol, 2.5 g of n-propyltrimethoxysilane and 2.5 g of methyltrimethoxysilane is added to a mixture of 200 ml of 2-propanol, 150 ml of deionized water and 30 g of 25% weight-% aqueous ammonia solution. The combined mixtures are stirred vigorously for 24 h at room temperature. Then, 5 g of tetraethoxysilane in 50 ml of 2-propanol are added. Afterwards this reaction mixture is stirred for 24 h and then centrifuged.

The residue is dispersed in ethyl acetate, washed and centrifuged thrice, thereafter no starting material is found in the supernatant. The thus obtained residue is dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2dd

Extended Silica-Core-Particles

A mixture of 0.25 g of the modified perylene of example 2c as described above, combined first with 80 ml of DMA, 100 ml of 2-propanol, 2.5 g of n-propyltrimethoxysilane and 2.5 g of methyltrimethoxysilane is added to a mixture of 200 ml of 2-propanol, 150 ml of deionized water and 30 g of 25% by weight aqueous ammonia solution. The combined mixtures are stirred vigorously for 4 h at room temperature. Then, 5 g of tetraethoxysilane (Aldrich, 99.99%) in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2e

A mixture of 0.25 g of the modified perylene of example 2c as described above, combined first with 50 ml of DMA, 80 ml of 2-propanol, 2.5 g of n-propyltrimethoxysilane and 2.5 g of methyltrimethoxysilane is added to a mixture of 100 ml of 2-propanol and 30 g of 25% by weight aqueous ammonia solution. The combined mixtures are stirred vigorously for 24 h at room temperature. Then, 300 ml of water is added and this reaction mixture is stirred for 24 h and then centrifuged. The residue is washed with ethanol, water and dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture consisting of 92.21% of a softening agent (Diisodecyl phthalate, DIDP, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed improved migration (grey scale 4.8).

Example 2f

A mixture of 0.25 g of the modified perylene of example 2c as described above, combined first with 50 ml of DMA, 80 ml of 2-propanol, 2.5 g of octadecyltriethoxysilane (Aldrich) is added to a mixture of 100 ml of 2-propanol and 30 g of 25% by weight aqueous ammonia solution. The combined mixtures are stirred vigorously for 24 h at room temperature. Then, 300 ml of water is added dropwise during 2 h and this reaction mixture is stirred for 24 h and then centrifuged. The residue is washed with ethanol, water and dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture consisting of 92.21% of a softening agent (Diisodecyl phthalate, DIDP, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed improved migration (grey scale 4.7).

Example 2g

Silica-Core-Shell Particles;
Perylene-bis-Imide-Silane Silica-Nanoparticles

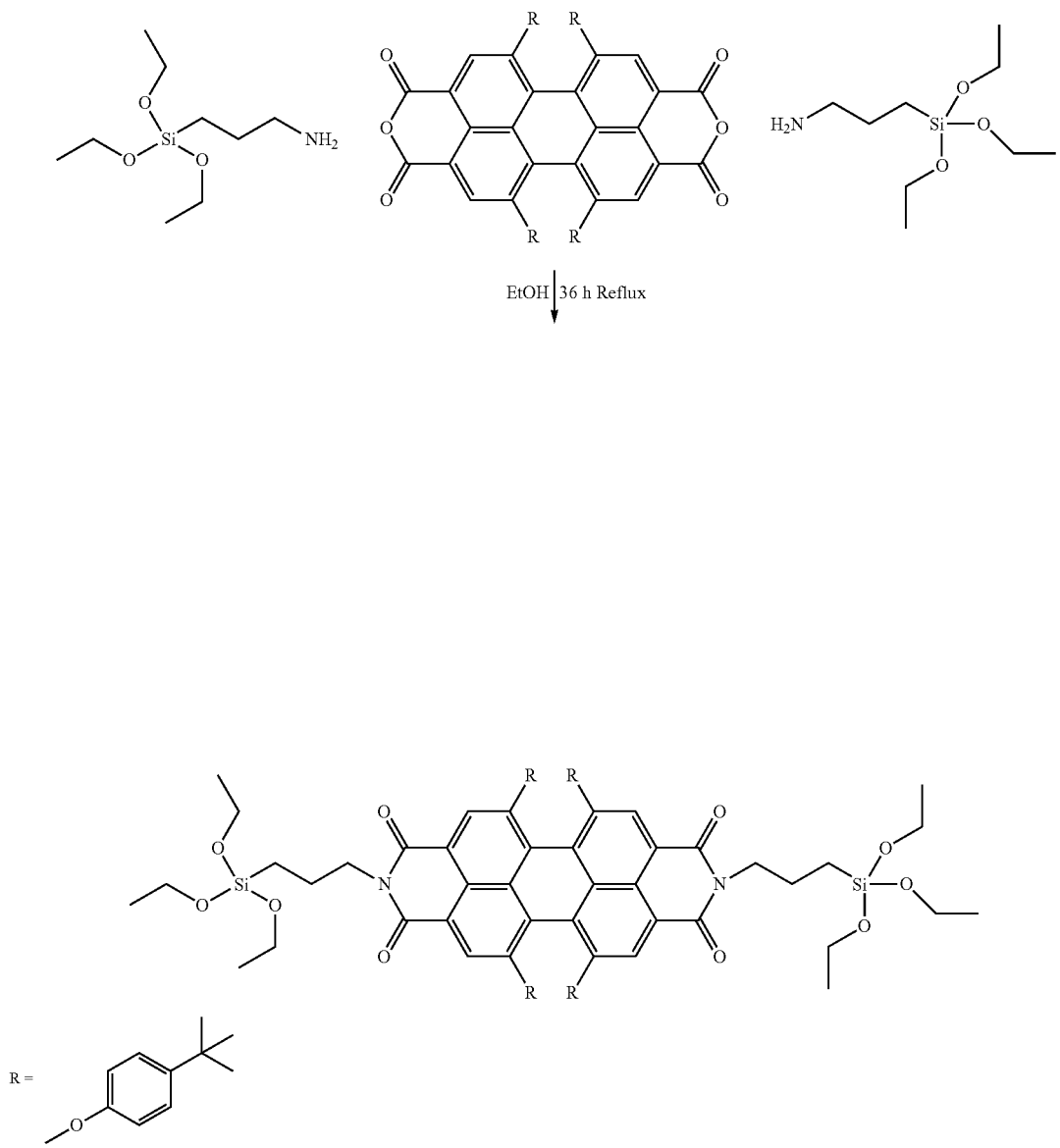

(a) Functionalizing a perylene derivative (see e.g.: US2008029739; *Chem. Mater.* 2000, 12, 352-362 M. Schneider, K. Muellen)

A mixture of 1,6,7,12-tetra(4'-t-butylphenoxy)-3,4,9,10-perylene tetracarboxylic dianhydride (1.7 g, 2 mmol) and 150 ml of dry ethanol is stirred for ½ h under an argon atmosphere, then it is heated to reflux (79° C.). Thereafter, 3.542 g (16 mmol) of (3-aminopropyl)-triethoxysilane (APTES) are added dropwise. The reaction mixture is stirred for 36 h at reflux conditions and under an inert atmosphere. After the mixture is cooled to room temperature, the precipitate is collected by suction filtration, washed with methanol and recrystallized from dichlormethane/methanol and dried in vacuum. A dark violet product is obtained in 79% yield.

(b) A mixture of 0.25 g of the modified perylene derivative obtained above, 100 ml of dimethylacetamide ("DMA"), 100 ml of 2-propanol and 5 g of n-propyltrimethoxysilane is added to a mixture of 200 ml of 2-propanol, 150 ml of deionized water and 30 g of 25% by weight aqueous ammonia solution. The combined mixtures are stirred vigorously for 24 h at room temperature. Then 5 g of tetraethoxysilane in 50 ml of 2-propanol are added. Afterwards this reaction mixture is stirred for additional 24 h and then centrifuged. The residue is dispersed in ethyl acetate, washed and centrifuged thrice until no starting material is found in the supernatant. The thus obtained residue is dried during 24 h in an atmosphere under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2gg

Extended Silica-Core-Particles

A mixture of 0.25 g of the modified perylene of example 2 g as described above, combined first with 100 ml of DMA, 100 ml of 2-propanol and 5 g of n-propyltrimethoxysilane is added to a mixture of 200 ml of 2-propanol, 150 ml of deionized water and 30 g of 25% by weight aqueous ammonia solution. The combined mixtures are stirred vigorously for 4 h at room temperature. Then 5 g of tetraethoxysilane (Aldrich, 99.99%) in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2ggg

Extended Silica-Core-Particles with Reduced Dye Loading

A mixture of 50 mg of the modified perylene of example 2 g as described above, combined first with 80 ml of DMA, 100 ml of 2-propanol and 5 g of n-propyltrimethoxysilane is added to a mixture of 200 ml of 2-propanol, 150 ml of deionized water and 30 g of 25% by weight aqueous ammonia solution. The combined mixtures are stirred vigorously for 4 h at room temperature. Then 5 g of tetraethoxysilane (Aldrich, 99.99%) in 30 ml of ethanol are added.

Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 2h

Silica-Core-Shell Particles

A mixture of 0.25 g of the modified perylene of example 2g as described above, combined first with 100 ml of DMA, 100 ml of 2-propanol, 2.5 g of n-propyltrimethoxysilane and 2.5 g of methyltrimethoxysilane is added to a mixture of 200 ml of 2-propanol, 150 ml of deionized water and 30 g of 25% weight-% aqueous ammonia solution. The combined mixtures are stirred vigorously for 24 h at room temperature. Then, 5 g of tetraethoxysilane in 50 ml of 2-propanol are added. Afterwards this reaction mixture is stirred for 24 h and then centrifuged. The residue is dispersed in ethyl acetate, washed and centrifuged thrice, thereafter no starting material is found in the supernatant. The thus obtained residue is dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed no migration (grey scale 5).

Example 2hh

Extended Silica-Core-Particles

A mixture of 0.25 g of the modified perylene of example 2c as described above, combined first with 100 ml of DMA, 100 ml of 2-propanol, 2.5 g of n-propyltrimethoxysilane and 2.5 g of methyltrimethoxysilane is added to a mixture of 200 ml of 2-propanol, 150 ml of deionized water and 30 g of 25% by weight aqueous ammonia solution. The combined mixtures are stirred vigorously for 4 h at room temperature. Then, 5 g of tetraethoxysilane (Aldrich, 99.99%) in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed no migration (grey scale 5).

Example 2i

A mixture of 0.1 g of the modified perylene of example 2g as described above, combined first with 50 ml of DMA, 80 ml of 2-propanol, 2.5 g of octadecyltriethoxysilane (Aldrich) is added to a mixture of 100 ml of 2-propanol and 30 g of 25% by weight aqueous ammonia solution. The combined mixtures are stirred vigorously for 24 h at room temperature. Then, 300 ml of water is added dropwise during 2 h and this reaction mixture is stirred for 24 h and then centrifuged. The residue is washed with ethanol, water and dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture consisting of 92.21% of a softening agent (Diisodecyl phthalate, DIDP, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed improved migration (grey scale 4.0).

Example 3

Preparation of the Following Functionalized Dyestuff

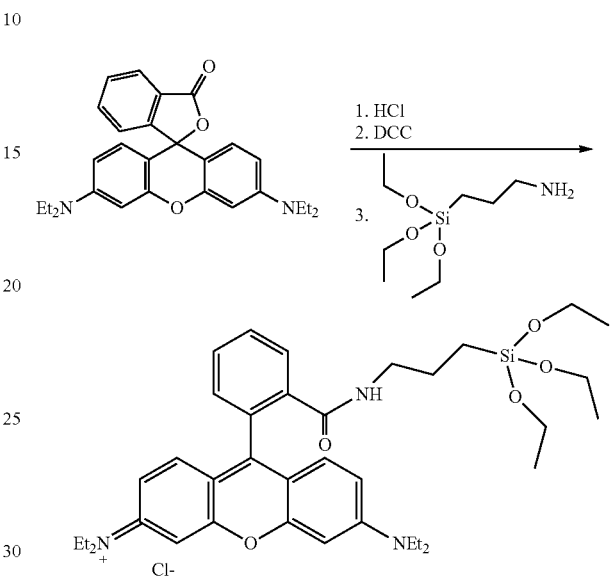

150 µl of concentrated HCl (37%, Merck) are added to 100 mg of Rhodamine B Base in 3 ml of deionized water. Then the mixture is evaporated to dryness. To the obtained dried residue 5 ml of dimethylformamide (Aldrich, 99.9%) are added. Thereafter, 100 mg of dicyclohexylcarbodiimide ("DCC") and 2 g of (3-aminopropyl)triethoxysilane are added. The reaction mixture is then stirred until termination of the reaction at room temperature and finally centrifuged. The obtained red solution is kept in the dark at a temperature below 7° C. Part of the product is isolated by chromatography with ethyl acetate/methanol/pyridine 2:5:1. For further use, the reaction mixture is useful for reactions without any workup.

Example 3a

Preparation of Alumina Core-Shell Particles

To 10 mg of the fluorescent dye compound of example 3 as described above are added 200 ml of ethanol and 30 g of 25% by weight aqueous ammonia solution under vigorously stirring. After 24 h at room temperature under exclusion from light, 10 g of aluminium tri-isopropoxid (Aldrich, 99.99%) dissolved in 150 ml of 2-propanol (Aldrich, 99.9%) are added. The mixture is then stirred for additional 24 h, after which time the obtained core-shell particles are centrifuged. The residue is dispersed in ethanol, precipitated by addition of ethyl acetate, washed and centrifuged thrice until no starting material is found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture consisting of 92.21% of a softening agent (Diisodecyl phthalate, DIDP, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed improved migration (grey scale 5).

Example 3aa

Extended Alumina-Core Particles

To 10 mg of the fluorescent dye compound of example 3 as described above are added 200 ml of ethanol and 30 g of 25% by weight aqueous ammonia solution under vigorously stirring. After 4 h at room temperature under exclusion from light, 10 g of aluminium tri-isopropoxid (Aldrich, 99.99%) dissolved in 150 ml of 2-propanol (Aldrich, 99.9%) are added under vigorously stirring. The mixture is stirred for additional 24 h and the extended alumina-core particles are centrifuged. The residue is dispersed in ethanol, precipitated by addition of ethyl acetate, washed and centrifuged thrice until no starting material or unreacted compounds are found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture consisting of 92.21% of a softening agent (Diisodecyl phthalate, DIDP, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed improved migration (grey scale 5).

Example 3aaa

Extended Alumina-Core-Shell Particles

To 10 mg of the fluorescent dye compound of example 3 as described above are added 200 ml of ethanol and 30 g of 25% by weight aqueous ammonia solution under vigorously stirring. After 4 h at room temperature under exclusion from light, 5 g of aluminium tri-isopropoxid (Aldrich, 99.99%) dissolved in 100 ml of 2-propanol (Aldrich, 99.9%) are added. The mixture is stirred for additional 24 h at room temperature, then another 5 g of aluminium tri-isopropoxid (Aldrich, 99.99%) dissolved in 100 ml of 2-propanol (Aldrich, 99.9%) are added to the vigorously stirred solution. The mixture is stirred for additional 24 h at room temperature and the extended Alumina-core-shell particles are centrifuged. The residue is dispersed in ethanol, precipitated by addition of ethyl acetate, washed and centrifuged thrice until no starting material or unreacted compounds are found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed no migration (grey scale 5).

Example 3b

Alumina Core-Shell Particles (a) Functionalizing the Dyestuff

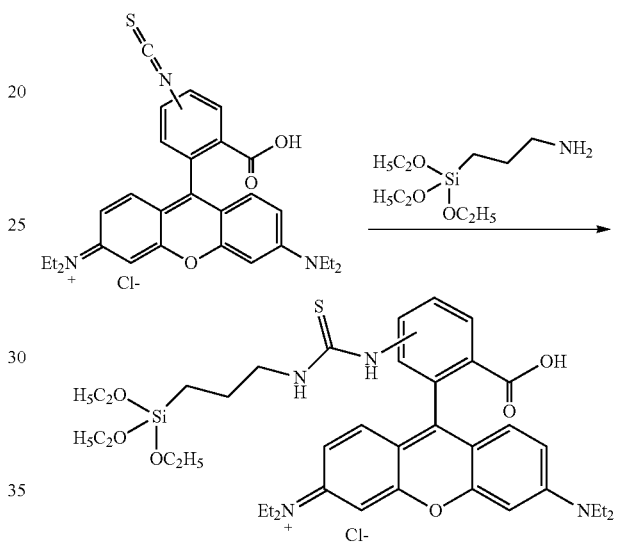

100 mg of tetraethylrhodamine isothiocyanate (Rhodamine B isothiocyanate, mixture of isomers obtained from Aldrich) are stirred in 40 ml of ethanol (99.9% Aldrich) with 2 g of 3-aminopropyltriethoxysilane for 48 h at room temperature under protection of light. Part of the reaction mixture is isolated by chromatography with ethyl acetate/methanol/pyridine 2:5:1. For further use, the reaction mixture is useful for reactions without any workup.

(b) Preparation of the Al-Core-Shell Particles

To 10 mg of the functionalized compound as described above under (a) are added 200 ml of ethanol and 30 g of 25% by weight aqueous ammonia solution under vigorously stirring. After 24 h at room temperature under exclusion from light, 15 g of aluminium tri-isopropoxid (Aldrich, 99.99%) dissolved in 200 ml of 2-propanol (Aldrich, 99.9%) are added. The mixture is then stirred for additional 24 h, after which time the obtained silica core-alumina-shell particles are centrifuged. The residue is dispersed in ethanol, precipitated by addition of ethyl acetate, washed and centrifuged thrice until no starting material is found in the supernatant.

The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 3bb

Extended Alumina-Core Particles

To 10 mg of the functionalized compound as described above under example 3b (a) are added 200 ml of ethanol and 30 g of 25% by weight aqueous ammonia solution under vigorously stirring. After 4 h at room temperature under exclusion from light, 10 g of aluminium tri-isopropoxid (Aldrich, 99.99%) dissolved in 150 ml of 2-propanol (Aldrich, 99.9%) are added under vigorously stirring. The mixture is stirred for additional 24 h and the extended alumina-core particles are centrifuged. The residue is dispersed in ethanol, precipitated by addition of ethyl acetate, washed and centrifuged thrice until no starting material are found in the supernatant. The thus obtained residue is dried 24 h under an atmosphere of reduced pressure (70 hPa) at a temperature of 60° C. Part of the obtained residue is stored as dispersion in ethanol.

0.4 g of the obtained product and 26.6 g of PVC (EVIPOL®SH 7020, EVC GmbH, Frankfurt/Main), 14.6 g of a mixture consisting of 92.21% of a softening agent (Diisodecyl phthalate, DIDP, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed improved migration (grey scale 5).

Example 3bbb

Extended Alumina-Core-Shell Particles

To 10 mg of the functionalized compound as described above under example 3b (a) are added 200 ml of ethanol and 30 g of 25% by weight aqueous ammonia solution under vigorously stirring. After 4 h at room temperature under exclusion from light, 5 g of aluminium tri-isopropoxid (Aldrich, 99.99%) dissolved in 100 ml of 2-propanol (Aldrich, 99.9%) are added under vigorously stirring. The mixture is stirred for additional 24 h at room temperature, then 5 g of aluminium tri-isopropoxid (Aldrich, 99.99%) dissolved in 100 ml of 2-propanol (Aldrich, 99.9%) are added under vigorously stirring. The mixture is stirred for additional 24 h at room temperature; thereafter the extended Alumina-core-shell particles are centrifuged. The residue is dispersed in ethanol, precipitated by addition of ethyl acetate, washed and centrifuged thrice until no starting material is found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 3c

Triple-Dye-Doped Alumina Core-Shell Particles (a) Functionalizing of the Fluoresceine 5(6)-Isothiocyanate Dyestuff A mixture of 5 mg of fluoresceine 5- and 6-isothiocyanate (90%, obtained from Aldrich) 4 ml of ethanol (Aldrich, 99.9%) and 100 mg of 3-aminopropyltriethoxysilane are stirred for 48 h at room temperature under protection against light. Part of the product is isolated by evaporation of the solvent; the rest is left in the reaction mixture for further reaction.

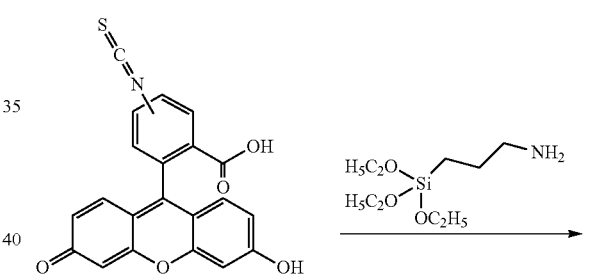

(b) Functionalizing of 5- and -6-Carboxy-X-Rhodamine Succinimidyl Ester Dyestuff A mixture of 5 mg of a 5- and 6-carboxy-X-rhodamine succinimidyl ester (available from Invitrogen/Molecular Probes), 4 ml of anhydrous DMF (Aldrich, 99.9%) and 100 mg of 3-aminopropyltriethoxysilane are stirred for 48 h at room temperature under protection against light. Part of the product is isolated by evaporation of the solvent; the rest is left in the reaction mixture for further reaction.

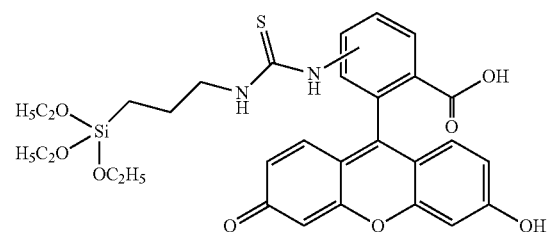

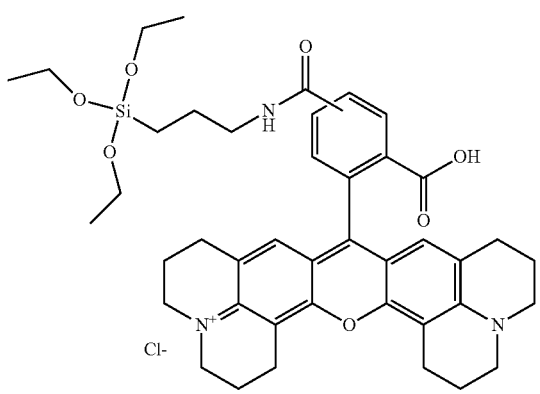

(c) Functionalizing of the 5- and 6-Carboxyrhodamine 6G Succinimidyl Ester Dyestuff A mixture of 5 mg of 5- and 6-carboxyrhodamine 6G succinimidyl ester,

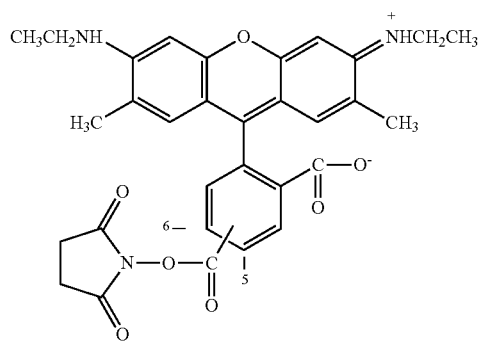

4 ml of anhydrous DMF (Aldrich, 99.9%) and 100 mg of 3-aminopropyltriethoxysilane are stirred for 48 h at room temperature under protection against light yielding

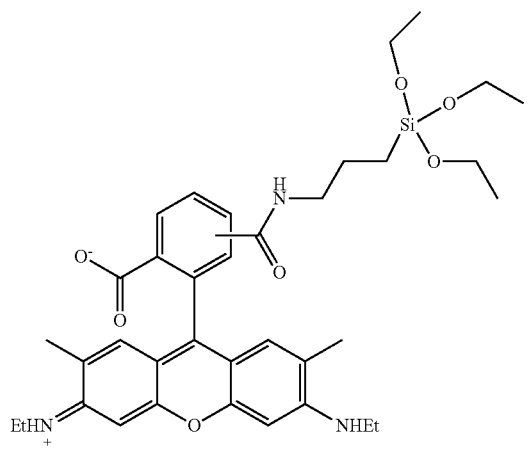

Part of the product is isolated by evaporation of the solvent, the rest is left in the reaction mixture for further reaction.

(d) Preparation of the Triple-Dye-Doped Alumina Core-Shell Particles

A mixture of 5 mg of each of the above under (a) to (c) prepared functionalized dyes in 150 ml of ethanol (96% Merck) is added to a mixture of 150 ml of ethanol, 30 g of 25% by weight of ammonia (from FLUKA) and 100 ml of water under vigorously stirring. After 24 h at room temperature under protection against light, 15 g of aluminium tri-isopropoxid (Aldrich, 99.99%) dissolved in 100 ml of 2-propanol (Aldrich, 99.9%) are added. The mixture is then stirred for additional 24 h, after which time the obtained alumina core-shell particles are centrifuged. The residue is dispersed in ethanol, precipitated by addition of ethyl acetate, washed and centrifuged thrice until no starting material is found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 3cc

Extended Alumina-Core-Particles

A mixture of 5 mg of each of the above under example 3c (a) to (c) prepared functionalized dyes in 150 ml of ethanol (96% Merck) is added to a mixture of 150 ml of ethanol, 30 g of 25% by weight of ammonia and 100 ml of water under vigorously stirring. After 4 h at room temperature under exclusion from light, 15 g of aluminium tri-isopropoxid (Aldrich, 99.99%) dissolved in 200 ml of 2-propanol (Aldrich, 99.9%) are added under vigorously stirring. The mixture is stirred for additional 24 h and the extended alumina-core particles are centrifuged. The residue is dispersed in ethanol, precipitated by addition of ethyl acetate, washed and centrifuged thrice until no starting material are found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 3ccc

Extended Alumina-Core-Shell Particles

A mixture of 5 mg of each of the above under example 3c (a) to (c) prepared functionalized dyes in 150 ml of ethanol (96% Merck) is added to a mixture of 150 ml of ethanol, 30 g of 25% by weight of ammonia and 100 ml of water under vigorously stirring. After 4 h at room temperature under exclusion from light, 7.5 g of aluminium tri-isopropoxid (Aldrich, 99.99%) dissolved in 100 ml of 2-propanol (Aldrich, 99.9%) are added under vigorously stirring. The mixture is stirred for additional 24 h. Then another 7.5 g of aluminium tri-isopropoxid (Aldrich, 99.99%) dissolved in 100 ml of 2-propanol (Aldrich, 99.9%) are added under vigorously stirring. The mixture is stirred for additional 24 h and the extended alumina-core-shell particles are centrifuged. The residue is dispersed in ethanol, precipitated by addition of ethyl acetate, washed and centrifuged thrice until no starting material are found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 4

Silica Core-Shell Particles

A mixture of 10 mg of each fluorescent dye compound obtained as described above in examples 3c(a) (mixture of fluoresceine isothiocyanate dyestuff), example 3c(c) (mixture of 5- and 6-carboxyrhodamine 6G succinimidyl ester derivative) and example 3 (Rhodamine B-derivative) in 150 ml of ethanol (96% Merck) is added to a mixture of 200 ml of ethanol (96%, Merck), 30 g of 25% by weight of ammonia (from FLUKA) and 100 ml of water under vigorously stirring. After 24 h at room temperature under protection against light, 25 g of tetraethoxysilane (TEOS) dissolved in 100 ml of ethanol are added. This mixture is then stirred for additional 24 h and the obtained core-shell particles are centrifuged. The residue is dispersed in ethanol, precipitated by addition of ethyl acetate, washed and centrifuged thrice until no starting material or unreacted compounds are found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 4a

Extended Silica-Core-Particles

A mixture of 10 mg of each fluorescent dye compound obtained as described above in examples 3c(a) (mixture of fluoresceine isothiocyanate dyestuff), example 3c(c) (mixture of 5- and 6-carboxyrhodamine 6G succinimidyl ester derivative) and example 3 (Rhodamine B-derivative) in 150 ml of ethanol (96% Merck) is added to a mixture of 200 ml of ethanol (96%, Merck), 30 g of 25% by weight of ammonia (from FLUKA) and 100 ml of water under vigorously stirring. After 4 h at room temperature under exclusion against light, 25 g of tetraethoxysilane dissolved in 150 ml of ethanol is added to the vigorously stirred solution. This mixture is then stirred for additional 24 h at room temperature, and the extended silica-core particles are centrifuged. The residue is dispersed in ethanol, precipitated by addition of ethyl acetate, washed and centrifuged thrice until no starting material or unreacted compounds are found in the supernatant. The thus obtained residue is dried 24 h under an atmosphere of reduced pressure (70 hPa) at a temperature of 60° C. Parts of the obtained residue are stored as dispersion in ethanol.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 5

A Hybridized Fluorescent Whitening Agent (FWA)

(a) Functionalizing of a Reactive FWA According to the Following Reaction Scheme

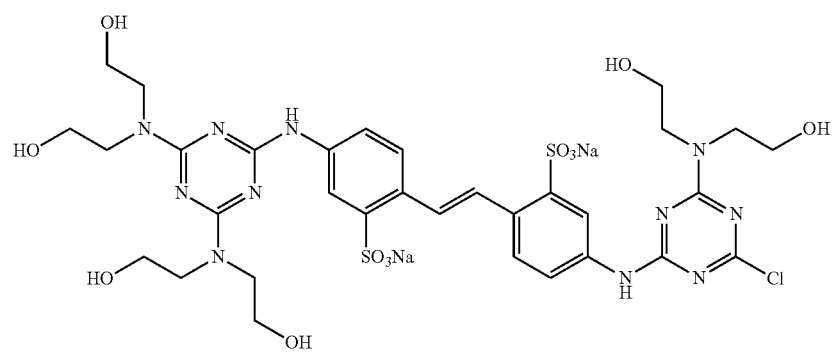
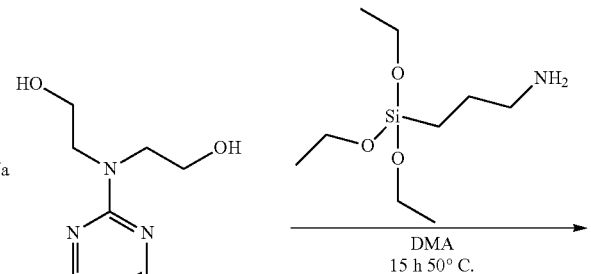

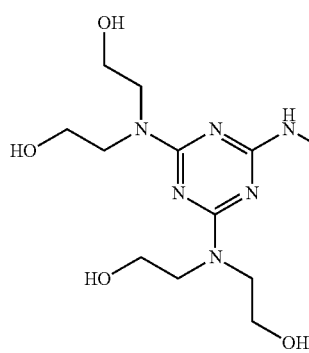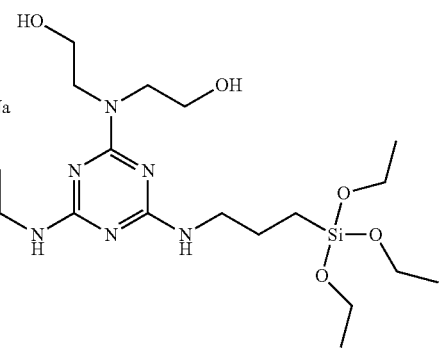

(a1) Preparation of the Reactive Fluorescent Whitening Agent

A solution of 64 g of 4-amino-4'-nitrostilbene-2,2'-disulfonic acid in 900 ml water is added to a mixture of 150 g methylethylketone, 173 g of ice and 30 g of cyanuric chloride. During the addition, the reaction temperature is kept below 10° C. by external cooling and the pH is kept between 4.5 and 5 by the addition of 53 ml of a 15% sodium carbonate solution in water. After the addition is complete, a solution of 18 g diethanolamine in 30 ml of water is added and the pH is adjusted to between 7 and 7.5 by the addition of 81 ml of 15% aqueous sodium carbonate solution. The reaction solution is then stirred for 1 h at 40° C. followed by 1 h at 60° C. 22 g diethanolamine are then added and the reaction solution is heated to 98° C. Simultaneously, the pH is adjusted to between 9 and 9.3 by the addition of 49 ml 4N aqueous sodium hydroxide solution, and 200 ml of the methylethylketone/water mixture is distilled off. The reaction solution is then stirred for 2 h at 98° C. The solution is cooled to room temperature, 200 g sodium chloride is added and the suspension stirred for 30 minutes, after which the formed precipitate is filtered off.

The product obtained in this manner (300 g) is then suspended in 400 ml of water and added portionwise to a mixture of 600 ml water, 40 g of iron and 10 ml of glacial acetic acid at 100° C. The mixture is stirred for 1.5 hours, rendered alkaline by 32% aqueous sodium hydroxide and filtered. The filtrate is treated with sodium dithionite, acidified with 125 ml concentrated hydrochloric acid and cooled to room temperature. The precipitate is filtered off, washed with 100 ml of water and dried in vacuum. Thus 94 g of yellow crystals are obtained. 36 g of this material is dissolved in water up to 360 ml. During 1 hour this solution is added to a mixture of 110 ml methylethylketone, 9.9 g cyanuric chloride, 130 ml water and 200 g ice. Simultaneously the pH is adjusted to between 4 and 4.5 by the addition of 12 ml of a 15% sodium carbonate solution.

After the addition of 6 g of diethanolamine in 25 ml water during 5 minutes, the mixture is heated to 40° C. for 40 minutes and to 60° C. for 30 minutes while the pH is adjusted to a value between 7 and 7.7 by addition of 15% sodium carbonate solution. Stirring is continued at 60° C. for another 30 minutes before heating further to 98° C. when 125 ml of the methylethylketone/water mixture is distilled off. After cooling to room temperature 100 g of sodium chloride is added and the mixture is stirred for 30 min. The formed precipitate is filtered off and dried in vacuum. Thus 66.1 g of yellow crystals are obtained (product contains 26.7% sodium chloride).

(a2) Functionalization of the Reactive FWA Obtained in Step (a1)

To 1 g of the above obtained reactive FWA (73.3% content, rest=NaCl) in 25 ml of dimethylacetamide at 60° C. 3.32 g of 3-aminopropyltriethoxysilane (15 mmol) are added over 30 min. After 2 h, the solution is cooled to room temperature. Part of the product is isolated by evaporation of the solvent.

(b) Silica Core-Shell Particles

A mixture of 1 g of the above functionalized FWA, 100 ml of 2-propanol, and 5 g of n-propyltrimethoxysilane is added to a mixture of 150 ml of 2-propanol, 100 ml of deionized water and 30 g of 25% by weight aqueous ammonia solution. The combined mixtures are stirred vigorously for 24 h at room temperature. Then, 5 g of tetraethoxysilane in 50 ml of 2-propanol are added. Afterwards this reaction mixture is stirred for 24 h and then centrifuged. The residue is dispersed in ethanol (80%), washed and centrifuged thrice, thereafter no starting material is found in the supernatant. The thus obtained residue is dried 24 h under an atmosphere of reduced pressure (70 hPa) at a temperature of 60° C.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed no migration (grey scale 5).

Example 5aa

Extended Silica-Core-Particles

A mixture of 1 g of the above functionalized FWA, 100 ml of 2-propanol and 5 g of n-propyltrimethoxysilane is added to a mixture of 150 ml of 2-propanol, 100 ml of deionized water and 30 g of 25% by weight aqueous ammonia solution. The combined mixtures are stirred vigorously for 4 h at room temperature. Then 5 g of tetraethoxysilane (Aldrich, 99.99%)

in 30 ml of ethanol are added. Afterwards this reaction mixture is stirred for 24 h and then centrifuged. The residue is dispersed in ethanol, precipitated by addition of ethyl acetate, washed and centrifuged thrice, thereafter no starting material is found in the supernatant. The thus obtained residue is dried 24 h under an atmosphere of reduced pressure (70 hPa) at a temperature of 60° C. Part of the residue is re-dispersed in ethanol for storage.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm$^2$, with heat stress during 30 min at 180° C.) showed no migration (grey scale 5).

Example 6.a

Seed particles from Reactive Red 218

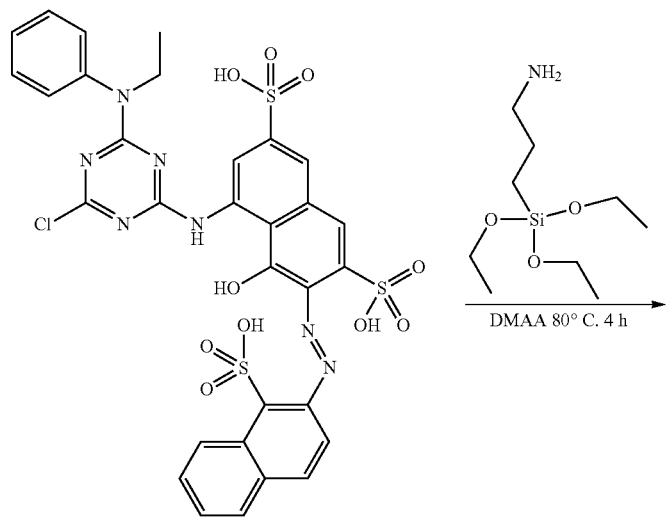

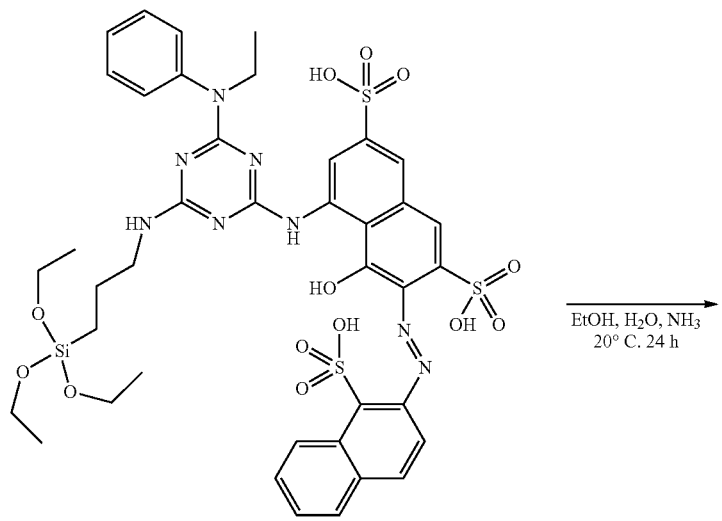

-continued
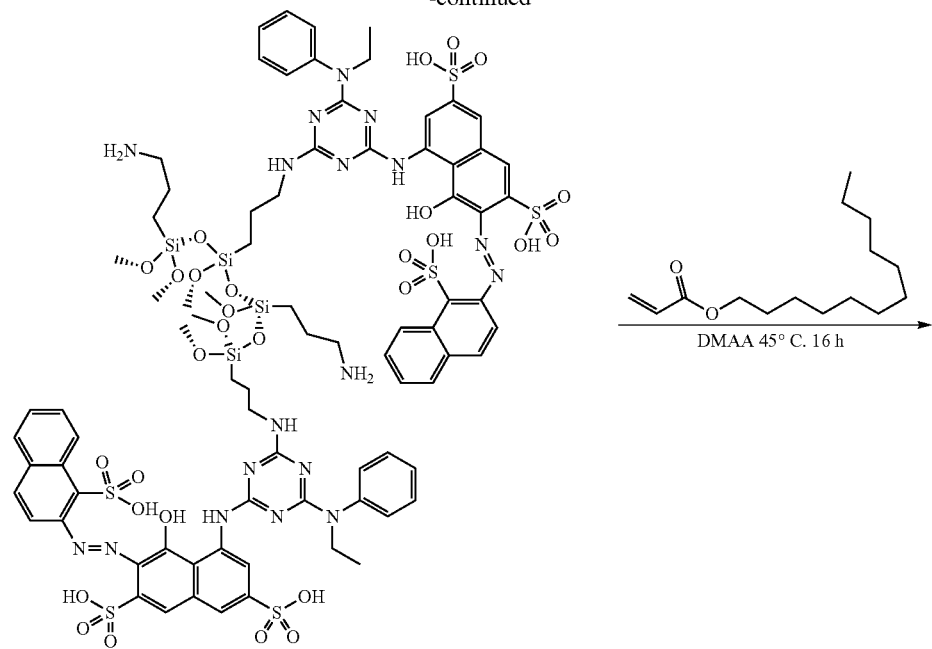
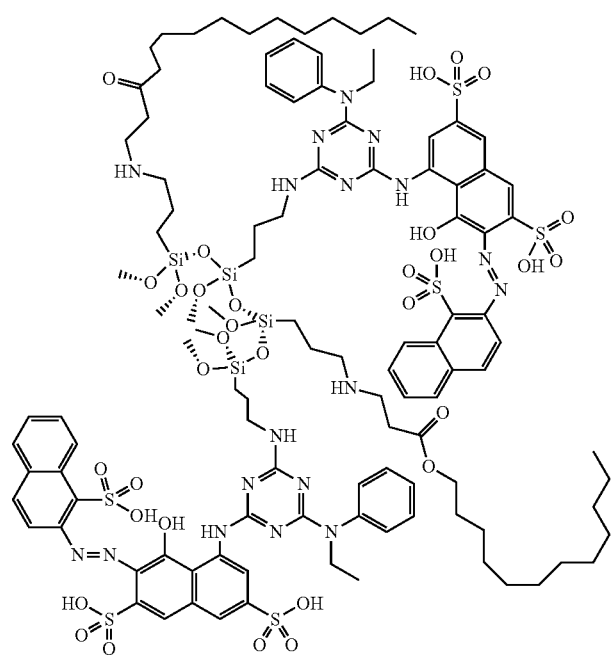

(a) Functionalizing Reactive Red 218

1 g of Reactive Red 218 (obtained as Cibacron®Red P-6B from Ciba) is dissolved in 25 ml of dimethylacetamide (DMA) at 60° C. 1.42 g of 3-aminopropyltriethoxy silane (5 eq.) are added over 30 min. After 4 h stirring at 80° C., the violet solution is cooled to room temperature. Part of the product is isolated by evaporation of the solvent.

(b) Preparation of Seed Particles

A mixture of 1 g of the above obtained functionalized Reactive Red 218 and 100 ml of 2-propanol is added to a mixture of 150 ml of 2-propanol, 50 ml of deionized water and 20 g of 25% by weight aqueous ammonia solution. The combined mixtures are stirred vigorously for 24 h at room temperature and then centrifuged. The residue is dispersed in ethanol (80%), washed and centrifuged thrice, thereafter no starting material is found in the supernatant.

The thus obtained residue is dried 24 h under an atmosphere of reduced pressure (70 hPa) at a temperature of 60° C.

(c) Surface Modification (Michael Addition) of the 3-Aminopropyl-Group with an Acrylate Derivative The above (b) obtained dark red residue is re-dispersed in 50 ml of dimethylacetamide, combined with 15 g of dodecylacrylate (Aldrich, techn. 90%) and stirred for 16 h at a temperature of 45° C. Then the mixture is diluted with 100 ml of ethyl acetate, washed and centrifuged thrice until no starting material is found in the supernatant. The desired product is obtained by evaporation of the solvent.

Part of the product is dispersed in dodecane (1% particle content w/w) for analyzing electrophoretic properties and particle size by DLS (Dynamic Light Scattering) with a MALVERN Zeta-Sizer:

| Example 6a | Data (20° C. in dodecane) |
|---|---|
| Zeta-Potential: | +53.9 mV |
| Mobility: | 0.0462 m²/Vs × 10⁻⁸ |
| Particle size (DLS): | 13 nm |

Example 6aa

Extended Silica-Seed-Particles

A mixture of 1 g of the above obtained functionalized Reactive Red 218 and 100 ml of 2-propanol is added to a mixture of 150 ml of 2-propanol, 50 ml of deionized water and 20 g of 25% by weight aqueous ammonia solution (from FLUKA). The combined mixtures are stirred vigorously for 4 h at room temperature. Then 0.4 g of tetraethoxysilane (Aldrich, 99.99%) dissolved in 20 ml of 2-propanol are added to the vigorously stirred solution. The mixture is stirred for additional 24 h at room temperature, and the extended silica-seed particles are centrifuged. The residue is dispersed in ethanol, precipitated by addition of ethyl acetate, washed and centrifuged thrice until no starting material or unreacted compounds are found in the supernatant. The thus obtained residue is dried 24 h under an atmosphere of reduced pressure (70 hPa) at a temperature of 60° C. Part of the residue is re-dispersed in ethanol for storage.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed no migration (grey scale 5).

Example 6b

Acid Yellow 95 Seed-Particles

(a) Functionalizing the Dyestuff According to the Following Scheme

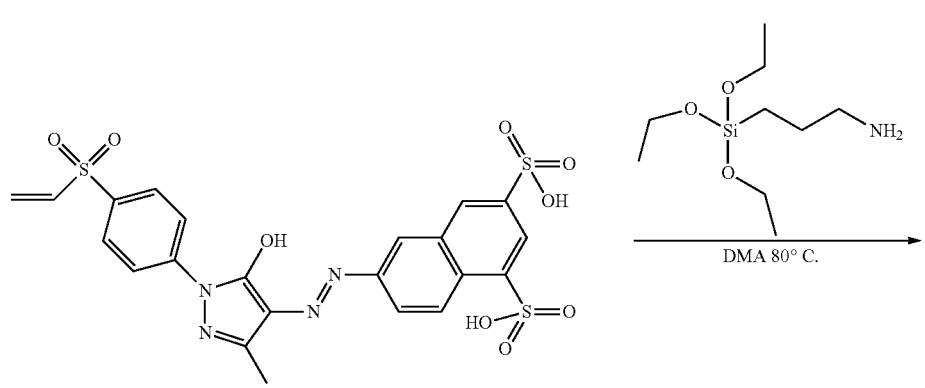

-continued

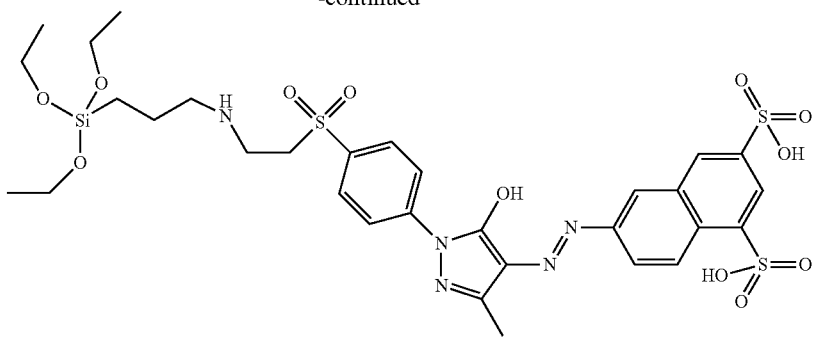

To 1 g of Acid Yellow 95 (obtained as Cibacron®Yellow D-6GS from Ciba Specialty Chemicals) in 25 ml of dimethylacetamide at a temperature of 60° C. 1.42 g of 3-aminopropyltriethoxysilane (5 eq.) are added over 30 min. After 4 h stirring at 80° C., the dark brown solution is cooled to room temperature. Part of the product is isolated by evaporation of the solvent.

(b) Preparation of Seed Particles

A mixture of 1 g of the above obtained functionalized Acid Yellow 95 and 100 ml of 2-propanol is added to a mixture of 150 ml of 2-propanol, 50 ml of deionized water and 20 g of 25% by weight aqueous ammonia solution (from FLUKA). The combined mixtures are stirred vigorously for 24 h at room temperature and then centrifuged. The residue is dispersed in ethanol (80%), washed and centrifuged thrice, thereafter no starting material is found in the supernatant. The thus obtained residue is dried 24 h under an atmosphere of reduced pressure (70 hPa) at a temperature of 60° C.

(c) Surface Modification (Michael Addition) of the 3-Aminopropyl-Group with an Acrylate Derivative The above (b) obtained residue is re-dispersed in 50 ml of dimethylacetamide, combined with 15 g of dodecylacrylate (Aldrich, techn. 90%) and stirred for 16 h at a temperature of 45° C. Then the mixture is diluted with 100 ml of ethyl acetate, washed and centrifuged thrice until no starting material is found in the supernatant. The desired product is obtained by evaporation of the solvent.

Example 6c

Reactive Blue Seed-Particles (a1) Functionalizing the Dye According to the Following Reaction Scheme

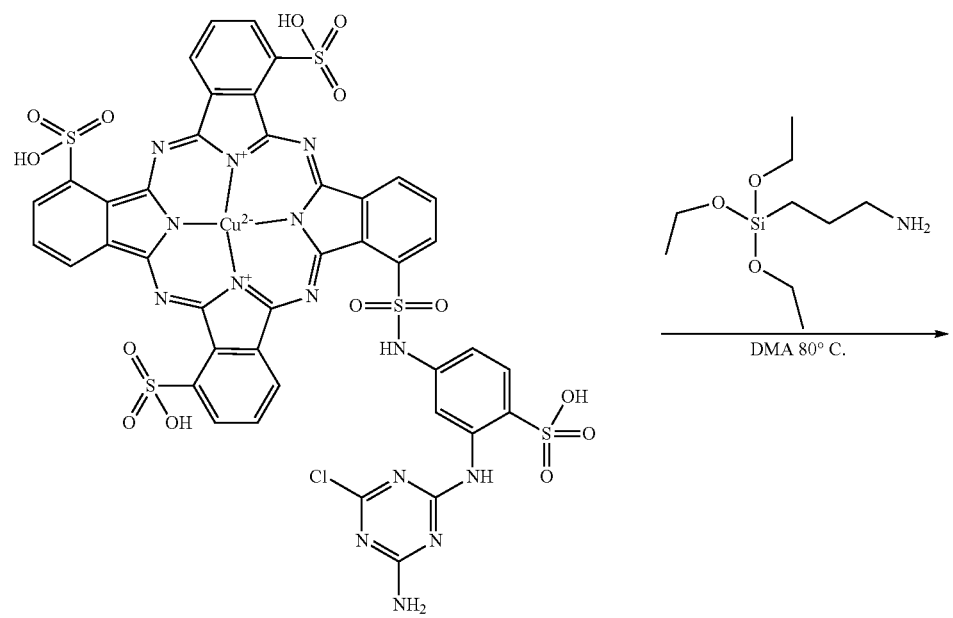

-continued

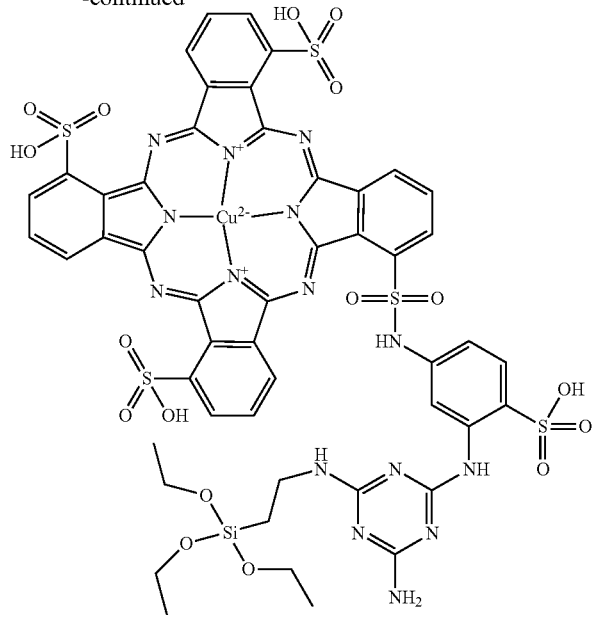

1 g of the above phthalocyanine dye (obtained as Reactive Dye Cibacron®Blue P-GR from Ciba Specialty Chemicals) is dissolved at 60° C. in 25 ml of dimethylacetamide. Then 1.42 g of 3-aminopropyltriethoxysilane (5 eq.) are added at 80° C. Parts of the obtained product are isolated by distillation of residual solvent.

(a2) Preparation of Seed Particles

A mixture of 1 g of the above obtained functionalized phthalocyanine and 100 ml of 2-propanol is added to a mixture of 150 ml of 2-propanol, 50 ml of deionized water and 20 g of 25% by weight aqueous ammonia solution (from FLUKA). The combined mixtures are stirred vigorously for 24 h at room temperature and then centrifuged. The residue is dispersed in ethanol (80%), washed and centrifuged thrice, thereafter no starting material is found in the supernatant. The thus obtained residue is dried 24 h under an atmosphere of reduced pressure (70 hPa) at a temperature of 60° C.

(a3) Surface Modification (Michael Addition) of the 3-Aminopropyl-Group with an Acrylate Derivative The above (b) obtained residue is re-dispersed in 50 ml of dimethylacetamide, combined with 15 g of dodecylacrylate (Aldrich, techn. 90%) and stirred for 16 h at a temperature of 45° C. Then the mixture is diluted with 100 ml of ethyl acetate, washed and centrifuged thrice until no starting material is found in the supernatant. The desired product is obtained by evaporation of the solvent.

Example 6d

Hair Dye Red Seed-Particles (a1) Functionalizing the Dyestuff According to the Following Reaction Scheme

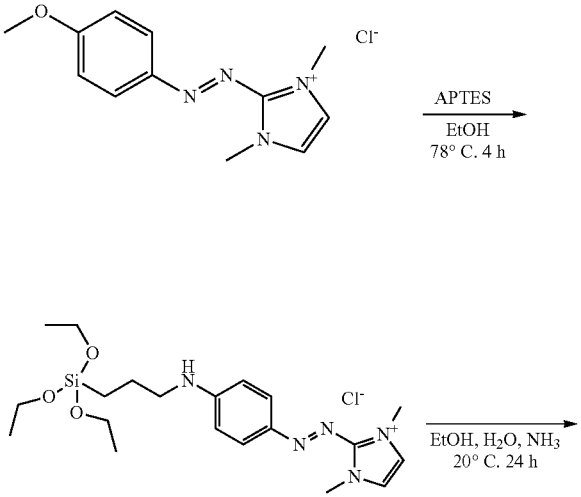

To a mixture of 0.75 g of the above diazo dye (CAS Registry Number 161328-92-3) and 70 ml of anhydrous ethanol a mixture of 2.9 g of 3-aminopropyltriethoxysilane and 20 ml of ethanol is added and the combined mixtures are heated to a temperature of 78° C. After 4 h, the dark red solution is cooled to room temperature. Parts of the product are isolated by evaporation of the solvent.

(a2) Preparation of the Desired Seed Particles

According to the Following Reaction Scheme

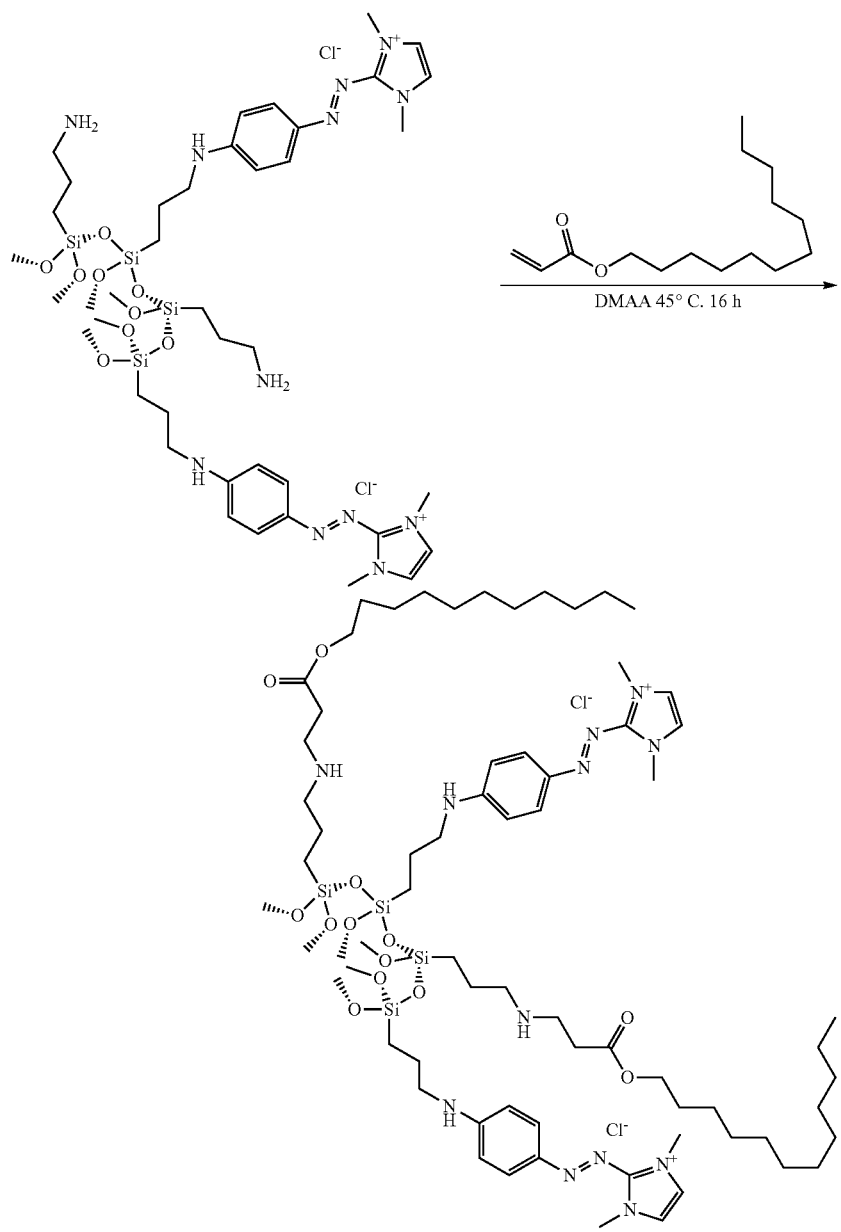

To 1 g of the above obtained functionalized dyestuff are added 150 ml of ethanol, 50 ml of water and 30 g of 25% by weight aqueous ammonia solution (from FLUKA) and the reaction mixture is then stirred vigorously for 24 h at room temperature. Thereafter, 50% of the solvent is evaporated in a rotary evaporator under an atmosphere of reduced pressure. The residue is mixed with 200 ml of ethyl acetate, centrifuged and the obtained residue washed and centrifuged thrice with ethyl acetate until no starting material is found in the supernatant. The thus obtained residue is dried 24 h under an atmosphere of reduced pressure (70 hPa) at a temperature of 60° C.

(a3) Surface Modification (Michael Addition) of the 3-Aminopropyl-Group with an Acrylate Derivative The above (a2) obtained dark red colored residue is dispersed in 50 ml of dimethylacetamide, combined with 15 g of dodecylacrylate (Aldrich, techn. 90%) and stirred for 16 h at a temperature of 45° C. Then the mixture is diluted with 100 ml of ethyl acetate, washed and centrifuged thrice until no starting material is found in the supernatant. The desired product is obtained by evaporation of the solvent.

The product is analyzed with a MALVERN Zeta-Sizer:

| Example 6d | Data (20° C. in dodecane) |
|---|---|
| Zeta-Potential: | −42.1 mV |
| Mobility: | 0.0362 m2/Vs × 10⁻⁸ |
| Particle size (DLS): | 7 nm |

Example 6dd

Extended Silica-Seed-Particles

To 1 g of the above obtained functionalized dyestuff according to example 6d(a2) are added 150 ml of ethanol, 50 ml of water and 30 g of 25% by weight aqueous ammonia solution (from FLUKA) and the reaction mixture is then stirred vigorously for 4 h at room temperature. Then 0.3 g of tetraethoxysilane (Aldrich, 99.99%) dissolved in 20 ml of 2-propanol are added to the vigorously stirred solution. The mixture is stirred for additional 24 h at room temperature, and the extended silica-seed particles are centrifuged. The residue is dispersed in ethyl acetate, washed and centrifuged thrice until no starting material is found in the supernatant. The thus obtained residue is dried 24 h under an atmosphere of reduced pressure (70 hPa) at a temperature of 60° C. Part of the residue is re-dispersed in ethyl acetate for storage.

0.4 g of the obtained product and 26.6 g of PVC (EVIPOL®SH 7020, EVC GmbH, Frankfurt/Main), 14.6 g of a mixture of stabilizer consisting of 92.21% of a softening agent (diisodecyl phthalate, Vestinol, Hüls Chemie), 4.19% of a rheology stabilizer (Rheoplast®39, Ciba) and 3.60% of a Ba/Zn stabilizer (Irgastab®BZ 561, Ciba) are calandered to a PVC-foil having a thickness of 0.5 mm and a content of 1% by weight of the corresponding sample. A migration test (measured during 24 h at 80° C. and a pressure of 1 kg/cm², with heat stress during 30 min at 180° C.) showed no migration (grey scale 4.8)

The invention claimed is:
1. Functionalized nanoparticles comprising:
    a core comprising a reaction product of a functionalized dyestuff of formula (1a) and a spacer of formula (1b), wherein the formula (1a) and the formula (1b) are defined below:

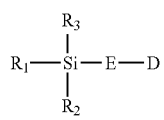

(1a)

wherein
    $R_1$ is $C_1$-$C_{18}$ alkoxy or —OH;
    $R_2$, $R_3$ independently from each other stand for $C_1$-$C_{18}$ alkoxy, $C_1$-$C_{18}$ alkyl or —OH,
    E stands for a direct bond or a bridging member,
    D is a chromophore, and

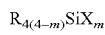

(1b)

wherein
    each $R_4$ represents a monovalent organic radical of from 1 to 24 carbon atoms, optionally substituted by a monovalent organic radical,
    X represents a group capable of undergoing hydrolysis and
    m is 0, 1, 2, 3 or 4; and
    a shell comprising a reaction product of a co-reactive compound (1c) selected from the group consisting of an organic silane, an organic alumina, an organic zirconia and an organic titania,
wherein the functionalized nanoparticles are obtained by
a) combining the functionalized dyestuff of the formula (1a),
    the spacer of the formula (1b),
    a catalyst, and
    optionally a solvent, at time $T_{SB}$, and
treating the obtained mixture until time $T_{SE}$, wherein ($T_{SE}$−$T_{SB}$) is chosen in the range of from 1 and 48 hours, at a temperature in the range of from 0 to 80° C.,
b) adding the co-reactive compound (1c) at time $T_{CC}$,
wherein $T_{CC}$ fulfils condition (a) $T_{CC} \geq T_{SE}$ or (b) (i) $T_{SB} < T_{CC} > T_{SE}$ and (ii) $T_{CC} \geq T_{SE}$ in case part of co-reactive compound (1c) is added before $T_{SE}$, and the other part after $T_{SE}$, and
treating the obtained respective reaction mixture for a period of time between 12 and 36 hours at a temperature between 0 and 80° C., and,
optionally, after isolating the thus obtained nanoparticles with well-known methods,
c) combining the nanoparticles with a polymer or,
d) polymerizing a monomer or monomer mixture in the presence of the nanoparticles.

2. Functionalized nanoparticles according to claim 1, wherein the co-reactive compound (1c) is added at time $T_{CC} \geq T_{SE}$ (condition (a)).

3. Functionalized nanoparticles according to claim 1, wherein the co-reactive compound (1c) is added at $T_{CC}$, wherein Tcc satisfies both (i) $T_{SB} < T_{CC} < T_{SE}$ and (ii) $T_{CC} \geq T_{SE}$ (condition (b)).

4. Functionalized nanoparticles according to claim 3, wherein between 10 to 90% by weight of the co-reactive organic compound (1c) is added before $T_{SE}$, but after $T_{SB}$, and the residual after or at time $T_{SE}$ (condition (b)).

5. Functionalized nanoparticles according to claim 1, wherein, in the compound of formula (1b), X stands for $C_1$-$C_{18}$alkoxy, whereby the alkyl chain may be interrupted by one or more oxygen or sulphur atoms.

6. Functionalized nanoparticles according to claim 1, wherein, in the compound of formula (1b), $R_4$ is a monovalent radical of from 1 to 12 carbon atoms, which is unsubstituted or substituted by a functional organic group selected from the group consisting of a mercapto, an epoxy, an acrylyl, a methacrylyl, an allyl, a vinyl, a halogeno and an amino group.

7. Functionalized nanoparticles according to claim 6, wherein, in the compound of formula (1b), X stands for $C_1$-$C_{18}$alkoxy, whereby the alkyl chain may be interrupted by one or more oxygen or sulphur atoms.

8. A composition comprising the functionalized nanoparticles according to claim 1 and an organic material.

9. Process for the manufacture of functionalized nanoparticles comprising the steps of:

a) combining a functionalized dyestuff of the formula (1a)

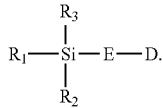
(1a)

wherein
$R_1$ stands for $C_1$-$C_{18}$alkoxy or —OH;
$R_2$, $R_3$ independently from each other stand for $C_1$-$C_{18}$alkoxy, $C_1$-$C_{18}$alkyl or —OH,
E stands for a direct bond or a bridging member,
D is a chromophore, and
a spacer of the formula (1b)

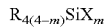
(1b)

wherein each $R_4$ represents a monovalent organic radical of from 1 to 24 carbon atoms, optionally substituted by a monovalent organic radical, X represents a group capable of undergoing hydrolysis and m is 0, 1, 2, 3 or 4;
a catalyst, and
optionally a solvent, at time $T_{SB}$, and
treating the obtained mixture until time $T_{SE}$, wherein ($T_{SE}$ – $T_{SB}$) is chosen in the range of from 1 and 48 hours, at a temperature in the range of from 0 to 80° C., b) adding a co-reactive compound (1c) selected from the group consisting of an organic silane, an organic alumina, an organic zirconia and an organic titania,
at time $T_{CC}$, wherein $T_{CC}$ fulfils condition (a) $T_{SB} < T_{CC} < T_{SE}$, (b) $T_{CC} \geq T_{SE}$ or (c) both (a) and (b) in case part of co-reactive compound (1c) is added before $T_{SE}$, and the other part after $T_{SE}$, and
treating the obtained respective reaction mixture for a period of time between 12 and 36 hours at a temperature between 0 and 80° C., and,
optionally, after isolating the thus obtained nanoparticles with well-known methods, c) combining the nanoparticles with a polymer or, d) polymerizing a monomer or monomer mixture in the presence of the nanoparticles.

* * * * *